(12) United States Patent
Hong et al.

(10) Patent No.: US 11,000,538 B2
(45) Date of Patent: May 11, 2021

(54) COMPOSITION FOR ENHANCING EXERCISE ABILITY OR ANTI-FATIGUE COMPRISING NOVEL GINSENOSIDE

(71) Applicant: AMOREPACIFIC CORPORATION, Seoul (KR)

(72) Inventors: Yong Deog Hong, Yongin-si (KR); Hyun Woo Jeong, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/666,586

(22) Filed: Oct. 29, 2019

(65) Prior Publication Data

US 2020/0131222 A1   Apr. 30, 2020

(30) Foreign Application Priority Data

Oct. 31, 2018 (KR) .................. 10-2018-0132417
Sep. 27, 2019 (KR) .................. 10-2019-0120088

(51) Int. Cl.

| A61K 31/7048 | (2006.01) |
| C07J 17/00 | (2006.01) |
| A61K 9/00 | (2006.01) |
| A61P 21/06 | (2006.01) |

(52) U.S. Cl.
CPC ........ *A61K 31/7048* (2013.01); *A61K 9/0029* (2013.01); *A61K 9/0053* (2013.01); *A61P 21/06* (2018.01); *C07J 17/005* (2013.01)

(58) Field of Classification Search
None
See application file for complete search history.

(56) References Cited

U.S. PATENT DOCUMENTS 8,440,632 B2 * 5/2013 Daley .................. A61P 9/02
514/26

FOREIGN PATENT DOCUMENTS

| CN | 102875628 A | 1/2013 |
| CN | 102924556 A | 2/2013 |
| KR | 10-178867 B1 | 11/1998 |
| KR | 10-1312389 B1 | 9/2013 |
| KR | 10-1568658 B1 | 11/2015 |
| KR | 10-2016-0086149 A | 7/2016 |
| WO | 2005/000245 A2 | 1/2005 |
| WO | 2005/000248 A2 | 1/2005 |
| WO | 2005/040189 A1 | 5/2005 |

OTHER PUBLICATIONS

Rho, T., Jeong, H. W., Hong, Y. D., Yoon, K., Cho, J. Y., & Yoon, K. D. (2020). Identification of a novel triterpene saponin from Panax ginseng seeds, pseudoginsenoside RT8, and its antiinflammatory activity. Journal of ginseng research, 44(1), 145-153. (Year: 2020).*

Cho, H. M., Kang, Y. H., Yoo, H., Yoon, S. Y., Kang, S. W., Chang, E. J., & Song, Y. (2014). Panax red ginseng extract regulates energy expenditures by modulating PKA dependent lipid mobilization in adipose tissue. Biochemical and biophysical research communications, 447(4), 644-648. (Year: 2014).*

Hsiao, C. Y., Hsu, Y. J., Tung, Y. T., Lee, M. C., Huang, C. C., & Hsieh, C. C. (2017). Effects of *Antrodia camphorata* and *Panax ginseng* supplementation on anti-fatigue properties in mice. Journal of Veterinary Medical Science, 17-0572. (Year: 2017).*

De Oliveira, A. C., Perez, A. C., Prieto, J. G., Duarte, I. D. G., & Alvarez, A. I. (2005). Protection of Panax ginseng in injured muscles after eccentric exercise. Journal of ethnopharmacology, 97(2), 211-214. (Year: 2005).*

Yang Jie, et al., "Semisynthesis and Cytotoxicity Evaluation of a Series of Ocotillol Type Saponins and Aglycones from 20(S)-Ginsenoside Rg2, Rh1, Protopanaxatriol and Their 20(R)-Epimers", Chem. Res. Chin. Univ., 2016, vol. 32, No. 1, pp. 35-40.

Si Young Cho, et al., "Effects of Chitooligosaccharide Lactate Salt on Sleep Deprivation-Induced Fatigue in Mice", Biol. Pharm. Bull., vol. 33, No. 7, pp. 1128-1132 (2010).

CAS RN : 2170771-84-1.

* cited by examiner

*Primary Examiner* — Dale R Miller
(74) *Attorney, Agent, or Firm* — Merchant & Gould P.C.

(57) ABSTRACT

The present specification relates to a composition containing novel (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof as an active ingredient. The composition exhibits an excellent exercise ability enhancing effect and anti-fatigue effect.

10 Claims, 24 Drawing Sheets

Chemical Formula: $C_{42}H_{72}O_{14}$
Exact Mass: 800.4922

1. Ginsenoside Rg1

Chemical Formula: $C_{42}H_{72}O_{13}$
Exact Mass: 784.4973

2. (20S)-Ginsenoside Rg2

Chemical Formula: $C_{48}H_{82}O_{18}$
Exact Mass: 946.5501

3. Ginsenoside Re

Chemical Formula: $C_{48}H_{82}O_{18}$
Exact Mass: 946.5501

4. Ginsenoside Rd

Chemical Formula: $C_{54}H_{92}O_{23}$
Exact Mass: 1108.6029

5. Ginsenoside Rb1

Chemical Formula: $C_{53}H_{90}O_{22}$
Exact Mass: 1078.5924

6. Ginsenoside Rb2

COMPOSITION FOR ENHANCING EXERCISE ABILITY OR ANTI-FATIGUE COMPRISING NOVEL GINSENOSIDE

CROSS-REFERENCE TO RELATED APPLICATION

This application claims priority to Korean Patent Application No. 10-2018-132417 filed on Oct. 31, 2018 and Korean Patent Application No. 10-2019-0120088 filed on Sep. 27, 2019, and all the benefits accruing therefrom under 35 U.S.C. § 119, the contents of which in its entirety are herein incorporated by reference.

BACKGROUND OF THE INVENTION

Field of the Invention

The present specification describes novel ginsenosides and compositions comprising the same.

Description of the Related Art

Ginseng (*Panax ginseng* C. A. Meyer) is a plant belonging to the genus *Panax* of the family Araliaceae. It has been used as herbal medicine from 2,000 years ago in Korea, China, Japan, etc.

As the representative physiologically active ingredients of ginseng, saponins, polysaccharides, peptides, sitosterols, polyacetylenes and fatty acids are known, and among them, saponins of ginseng are called ginsenosides. The effects and efficacies of ginseng comprise action on the central nervous system, anticarcinogenic action, anticancer activity, immunomodulatory action, antidiabetic action, liver function improving effect, action of improving cardiovascular disorders, anti-atherosclerotic action, blood pressure controlling action, action of improving menopausal disorder, effect on osteoporosis, anti-stress action, anti-fatigue action, antioxidant action, antiaging effect, etc. The ginsenoside has a large difference in its content and composition depending on the parts such as roots, leaves, fruits, flowers, seeds, etc. of ginseng, but the efficacy known as above is mostly about the ginseng root, namely, the root part of ginseng, and research on other parts of ginseng except ginseng root is insufficient With increasing interest in health and exercise, there is also a growing demand for supplements, functional foods or beverages that can quickly enhance exercise ability or provide energy for athletes as well as the general public. Along with this, protein supplements, carbohydrate supplements, or anabolic steroids, caffeine, etc. are known as components for increasing exercise ability, but such compounds may have side effects when taken, so their use is limited. Accordingly, the development of a product that can effectively supply energy to the human body without side effects on the human body is required.

CITATION LIST

Patent Literature

Patent Literature 1: Korean Patent Application Publication No. 10-2016-0086149

Non-Patent Literature

Non-Patent Literature: Cho et al., Biol Pharm Bull 33(7): 1128

SUMMARY OF THE INVENTION

In one aspect, the technical problem of the present invention is to provide a composition comprising a novel ginsenoside having excellent exercise ability enhancing efficacy.

In one aspect, the technical problem of the present invention is to provide a composition comprising a novel ginsenoside having excellent anti-fatigue efficacy.

In one aspect, the present disclosure provides a composition for enhancing exercise ability or anti-fatigue comprising (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof as an active ingredient.

In one aspect, the present disclosure may provide a composition comprising a novel ginsenoside, a pharmaceutically acceptable salt thereof, a hydrate or solvate thereof having an excellent effect on exercise ability enhancement and anti-fatigue.

DETAILED DESCRIPTION OF THE PREFERRED EMBODIMENTS

Figure 1:
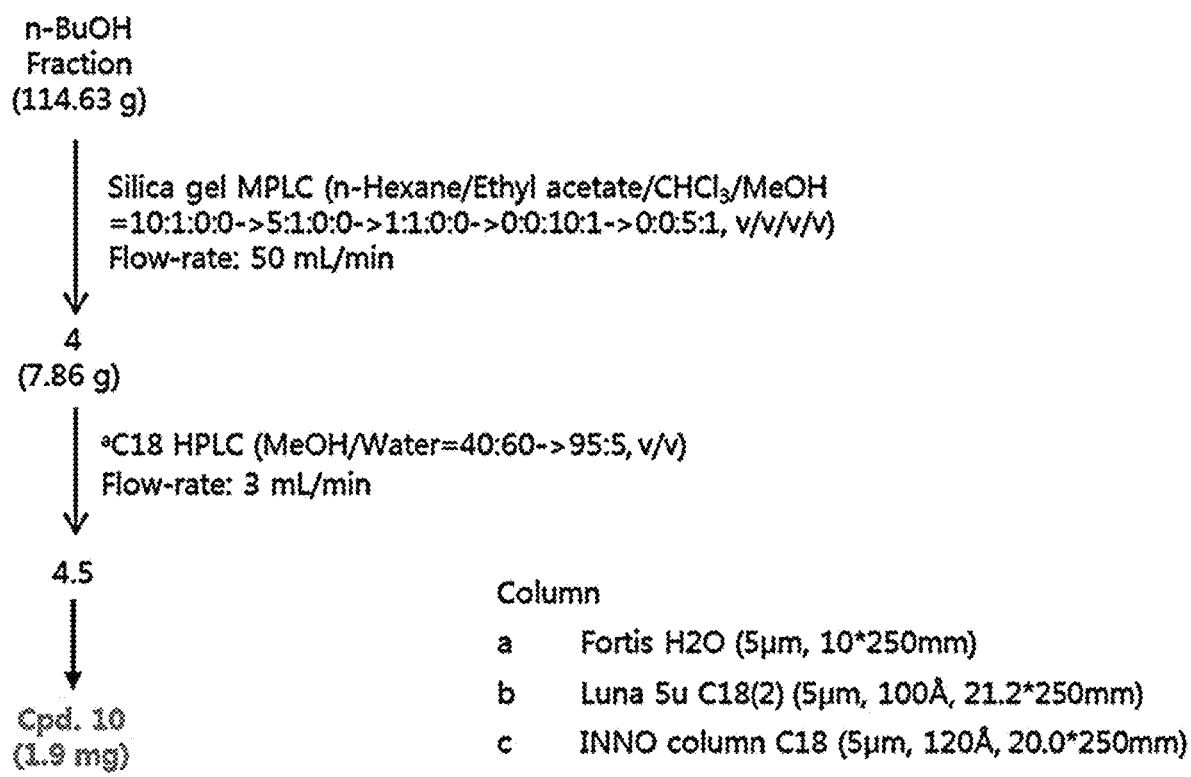
FIG. 1 is a diagram illustrating an isolation process of a novel ginsenoside (Cpd. 10) of the present disclosure among the compounds fractionated from ginseng seed extract.

Hereinafter, embodiments of the present disclosure will be described in more detail with reference to the accompanying drawings. However, the technology described in the present disclosure is not limited to the embodiments described herein and may be embodied in other forms. It is to be understood that the embodiments introduced herein are provided so that the disclosure can be made thorough and complete, and that the spirit of the present disclosure can be fully conveyed to those skilled in the art. In order to clearly express each constituent in the drawings, the size, such as the width or thickness, etc. of the constituent, is shown to be somewhat enlarged. In addition, although only a part of the constituents are shown for convenience of explanation, those skilled in the art will be able to easily understand the rest parts of the constituents. In addition, those having ordinary skill in the pertinent field may implement the spirit of the present disclosure in various other forms without departing from the technical spirit of the present disclosure.

In one embodiment, the present disclosure may provide a composition for enhancing exercise ability or anti-fatigue comprising a novel ginsenoside, a pharmaceutically acceptable salt thereof, a hydrate or a solvate thereof as an active ingredient.

In one embodiment, the ginsenoside is a novel triterpene saponin, and is (20S,24R)-6-O-β-D-glucopyranosyl(1→2)-β-D-glucopyranoside-dammar-3-one-20,24-epoxy-6a,12b,25-triol.

One embodiment may provide a use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof for use in the preparation of a composition for enhancing exercise ability or anti-fatigue.

One embodiment may provide a method of enhancing exercise ability or anti-fatigue comprising administering (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof in an effective amount to a subject in need thereof.

One embodiment may provide (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof as an active ingredient for use in a composition for enhancing exercise ability or anti-fatigue. In addition, a non-therapeutic use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof as an active ingredient for enhancing exercise ability or anti-fatigue.

As used herein, the term "pharmaceutically acceptable" refers to those that can be approved or was approved by the government or equivalent regulatory agencies for use in animals, more specifically in humans, by avoiding significant toxic effects when used in conventional medicinal dosage, or those recognized as being listed in the pharmacopoeia or described in other general pharmacopoeia.

As used herein, the term "pharmaceutically acceptable salt" refers to a salt according to one aspect of the present disclosure that is pharmaceutically acceptable and possesses the desired pharmacological activity of the parent compound. The salts comprise (1) acid addition salts, formed with inorganic acids such as hydrochloric acid, hydrobromic acid, sulfuric acid, nitric acid, phosphoric acid, or the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, or the like; or (2) salts formed when an acidic proton present in the parent compound is substituted.

As used herein, the term "hydrate" refers to a compound to which water is bound, and is a broad concept comprising an inclusion compound having no chemical bonding force between water and the compound.

As used herein, the term "solvate" refers to a compound of higher order produced between molecules or ions of a solute and molecules or ions of a solvent.

In one embodiment, the molecular formula of ginsenoside is $C_{42}H_{70}O_{15}$, and has the following chemical structure.

[Formula 1]

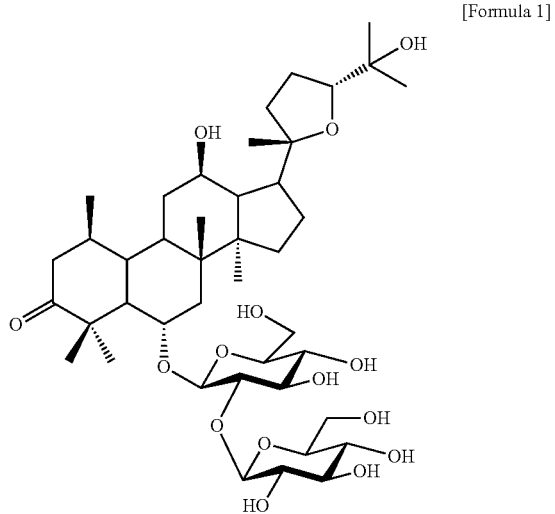

In the present specification, the novel ginsenosides are named "pseudoginsenoside $RT_8$" or "PG-$RT_8$."

In one embodiment, the ginsenoside may be isolated from the ginseng seed extract, but is not limited thereto. In one embodiment, the ginseng of the ginseng seed is *Panax ginseng* C. A. Meyer.

As used herein, the term "isolation" is meant to comprise those extracted or fractionated from ginseng seed extract, and may use water, organic solvents, or the like, and any method known to those skilled in the art may also be applied. The fraction may be performed after the extraction.

As used herein, the term "extract" means a substance obtained by extracting a component contained inside of a natural substance, regardless of the extracted method or ingredients.

The term is used in a broad sense comprising, for example, all of those obtained by extracting a component soluble in a solvent from a natural substance using water or an organic solvent, extracting only a specific component of a natural substance, or the like.

As used herein, "fractions" comprise those obtained by fractionating a specific substance or extract using a certain solvent or those leftover after fractions, and extracting them again with a specific solvent. Fractional methods and extraction methods may be any method known to those skilled in the art.

In one embodiment, the ginsenoside may be isolated from ginseng seed methanol- and butanol-soluble extracts. Specifically, the ginsenoside may be detected and isolated by analyzing methanol- and butanol-soluble extracts of ginseng seed using HPLC-ESI-Q-TOF-MS. Not all triterpenes and steroidal saponins can be observed by HPLC-UV or HPLC-ELSD from ginseng seed crude extract because the main component of ginseng seed extract is lipid.

In one embodiment, the use for enhancing exercise ability may comprise the use for muscle regeneration, muscle augmentation, muscle strengthening, or the prevention or improvement of sarcopenia.

In one embodiment, the use for anti-fatigue may comprise the use for fatigue recovery or lactic acid metabolism control.

In one embodiment, the active ingredient may promote the production of mitochondria in myocytes, and promote lipid metabolism in myocytes, that is, fatty acid oxidation. In addition, the active ingredient may reduce the plasma lactate in blood produced by exercise. As a result, the present disclosure can effectively supply ATP (adenosine triphosphate), which is energy necessary for exercise, to myocytes while reducing muscle fatigue, thereby promoting exercise effect and lasting exercise for longer period of time.

As used herein, the term "prevention" refers to any action that inhibits or delays a desired symptom by administering a composition according to one embodiment of the present disclosure. As used herein, the term "treatment" refers to any action that improves or disappears a desired symptom or disease by administering a composition according to one embodiment of the present disclosure. As used herein, the term "improvement" refers to any action in which a desired symptom is improved or advantageously changed from before administration by administering a composition according to one embodiment of the present disclosure.

In one embodiment, the present disclosure may contain the active ingredient in an amount of 0.0001 to 99.9% by weight based on the total weight of the composition. Specifically, as one embodiment, the composition may contain the active ingredient in an amount of at least 0.0001% by weight, at least 0.0005% by weight, at least 0.001% by weight, at least 0.01% by weight, at least 0.1% by weight, at least 1% by weight, at least 2% by weight, at least 3% by weight, at least 4% by weight, at least 5% by weight, at least 6% by weight, at least 7% by weight, at least 8% by weight, at least 9% by weight, at least 10% by weight, at least 15% by weight, at least 20% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, at least 80% by weight, at least 85% by weight, at least 90% by weight, at least 95% by weight, or at least 99.9% by weight based on the total weight of the composition, but is not limited to the above range. In addition, as one embodiment, the composition may contain the active ingredient in an amount of 100% or less by weight, 99% or less by weight, 95% or less by weight, 90% or less by weight, 85% or less by weight, 80% or less by weight, 75% or less by weight, 70% or less by weight, 65% or less by weight, 60% or less by weight, 55% or less by weight, 50% or less by weight, 45% or less by weight, 40% or less by weight, 35% or less by weight, 30% or less by weight, 25% or less by weight, 20% or less by weight, 15% or less by weight, 10% or less by weight, 9% or less by weight, 8% or less by weight, 7% or less by weight, 6% or less by weight, 5% or less by weight, 4% or less by weight, 3% or less by weight, 2% or less by weight, 1% or less by weight, 0.5% or less by weight, 0.1% or less by weight, 0.01% or less by weight, 0.001% or less by weight or 0.0005% or less by weight based on the total weight of the composition, but is not limited to the above range.

The composition according to embodiments of the present disclosure may be a composition for external skin application comprising the active ingredient.

As used herein, "skin" means the tissue covering the body surface of an animal and is used in the broadest sense, comprising not only the tissue that covers the face or body but also the scalp and hair.

The composition according to the embodiments of the present disclosure may be a food composition comprising the active ingredient.

For example, it may be processed into functional foods such as fermented milk, cheese, yogurt, juice, probiotic and health food containing the active ingredient, and may be used in the form of various other food additives. In one embodiment, the composition may be a composition for health food. In one embodiment, the composition for health food may be formulated into pills, capsules, tablets, granules, caramels, drinks, or the like. In another embodiment, the composition may be processed in the form of liquid, powder, granules, tablets, tea bags, or the like. The composition may be administered by various methods such as simple drinking, injection administration, spray administration or squeeze administration, or the like. The composition may contain other components that can give a synergistic effect to the main effect within a range that does not impair the main effect of the present disclosure. For example, it may further comprise additives such as perfumes, pigments, fungicides, antioxidants, preservatives, moisturizers, thickeners, inorganic salts, emulsifiers and synthetic polymer materials, or the like for improving the physical properties. In addition, the composition may further comprise auxiliary components, comprising water-soluble vitamins, oil-soluble vitamins, polymer peptides, polysaccharides and seaweed extracts. The above components may be suitably selected and mixed by those skilled in the art depending on the formulation or purpose of use and may be added in an amount selected within the range that does not impair the object and effect of the present disclosure. For example, the above components may be added in an amount of 0.0001 to 99.9% by weight based on the total weight of the composition. In one embodiment, the dose of the food composition may be varied with age, sex and body weight of a subject, particular disease or pathological condition the subject has, severity of the disease or pathological condition, administration route, and the like. Determination of the dose considering these factors is within the level of those skilled in the art. For example, the dose may be at least 0.05 mg/kg/day or at least 1 mg/kg/day, or the dose may be at least 0.8 mg/kg/day or at least 4 mg/kg/day. In addition, the dose may be at most 10 g/kg/day, at most 100 mg/kg/day or at most 10 mg/kg/day. However, the dosage does not limit the scope of the present specification in any way.

The composition according to the embodiments of the present disclosure may be a pharmaceutical composition comprising the active ingredients. The pharmaceutical composition may further comprise a pharmaceutical adjuvant such as antiseptic, stabilizer, hydrating agent, emulsifying accelerator, salt and/or buffer for controlling osmotic pressure, etc. or other therapeutically useful substance.

In one embodiment, the pharmaceutical composition may be a formulation for oral administration. The formulation for oral administration may comprise, for example, tablet, pill, hard or soft capsule, liquid, suspension, emulsion, syrup, powder, dust, granule, pellet, or the like. These formulations may comprise, in addition to the active ingredient, a surfactant, a diluent (e.g., lactose, dextrose, sucrose, mannitol, sorbitol, cellulose or glycine) or a lubricant (e.g., silica, talc, stearic acid and magnesium or calcium salt thereof, or polyethylene glycol). The tablet may comprise a binder such as magnesium aluminum silicate, starch paste, gelatin, tragacanth, methyl cellulose, sodium carboxymethyl cellulose and polyvinylpyrrolidone, and may occasionally comprise a pharmaceutical additive such as a disintegrant, e.g. starch, agar, alginic acid or a sodium salt thereof, an absorbent, a colorant, a flavor, a sweetener, or the like. The tablet may be prepared according to the commonly employed mixing, granulation or coating method.

In one embodiment, the pharmaceutical composition may be a formulation for parenteral administration, and the formulation for parenteral administration may be rectal, topical, subcutaneous, transdermal dosage form. The formulation for parenteral administration may comprise, for example, injection, drop, ointment, lotion, gel, cream, spray, suspension, emulsion, suppository, patch, etc., but is not limited thereto.

In one embodiment, the dose of the pharmaceutical composition may be varied with the age, sex and body weight of a subject to be treated, particular disease or pathological condition be treated, severity of the disease or pathological condition, administration route and the judgment of a prescriber. Determination of the dose considering these factors is within the level of those skilled in the art. For example, the dosage may be at least 0.05 mg/kg/day or at least 1 mg/kg/day, or the dose may be at least 0.8 mg/kg/day or at least 4 mg/kg/day. In addition, the dose may be at most 10 g/kg/day, at most 100 mg/kg/day or at most 10 mg/kg/day. However, the dosage does not limit the scope of the present specification in any way.

Hereinafter, the present disclosure will be described in detail with reference to examples, comparative examples and test examples. These are only presented by way of example only to more specifically describe the present disclosure, and it is obvious to those skilled in the art that the scope of the present disclosure is not limited by these examples, comparative examples and test examples.

All experimental values below represent the average of values obtained by repeating experiments three or more times, and standard deviation (SD) is indicated by error bars. p values were calculated by one-way ANOVA and Dunnett test, and p values less than 0.05 were considered statistically significant.

[Example 1] Isolation of Ginsenosides

Fraction 5.5 kg of ginseng seed (seeds of *Panax ginseng*) was finely ground in a mixer to make a powder form, extracted with methanol, and then fractionated step by step using n-hexane, ethyl acetate, n-butanol, and the like. Lipids were mostly removed by n-hexane, and the lipids remaining in the ethyl acetate fraction were suspended in methanol:water=1:1 (v/v), stored in the freezer overnight, and then only the supernatant was taken. The lipids were removed once more using a centrifuge. 2.61 g of ethyl acetate fraction and 114.64 g of n-butanol fraction thus pretreated were fractionated through column and HPCCC (High Performance Counter-Current Chromatography) as follows.

Fraction Using Columns of n-Butanol Fractions and HPCCC 114.64 g of n-butanol fraction was fractionated by MPLC, and the solvent used then was n-hexane/ethyl acetate=10:1→5:1→1:1→$CHCl_3$/MeOH=10:1→5:1 (v/v) and flow rate was 50 mL/min. The above conditions were used to make a total of 12 subfractions, and the components contained in each fraction were separated again using HPCCC, HPLC (High-performance liquid chromatography), Sephadex LH-20 column, or the like. 16 compounds were investigated by identifying their structure using NMR (Nuclear magnetic resonance), UV (Ultraviolet rays), and MS (Mass spectrometry).

The 16 compounds isolated comprise ginsenoside Rg1 (compound 1), ginsenoside Rg2 (compound 2) and ginsenoside Re (compound 3), which are protopanaxatriol saponins; ginsenoside Rd (compound 4), ginsenoside Rb1 (compound 5) and ginsenoside Rb2 (compound 6), which are protopanaxadiol saponins; stigma-5-en-3-O-β-D-glucopyranoside (compound 7), stigma-5,24 (28)-dien-3-O-β-D-glucopyranoside (compound 8) and stigma-5,22-dien-3-O-β-D-glucopyranoside (compound 9), which are sterol glycosides; (20S,24R)-6-O-β-D-glucopyranosyl(1→2)-β-D-glucopyranoside-dammar-3-one-20,24-epoxy-6a,12b,25-triol (compound 10), a novel compound that is first isolated from nature as a novel ginsenoside according to an embodiment of the present disclosure; phenethyl alcohol β-D-xylopyranosyl(1→6)-β-D-glucopyranoside (compound 12) and Eugenyl β-gentiobioside (compound 13), which are phenolic glycosides; isorhamnetin 3-O-β-D-glucopyranoside (compound 15), which is flavonoid; and adenosine (compound 11), uracil (compound 14) and tryptophan (compound 16), which are primary metabolites.

Figure 2:
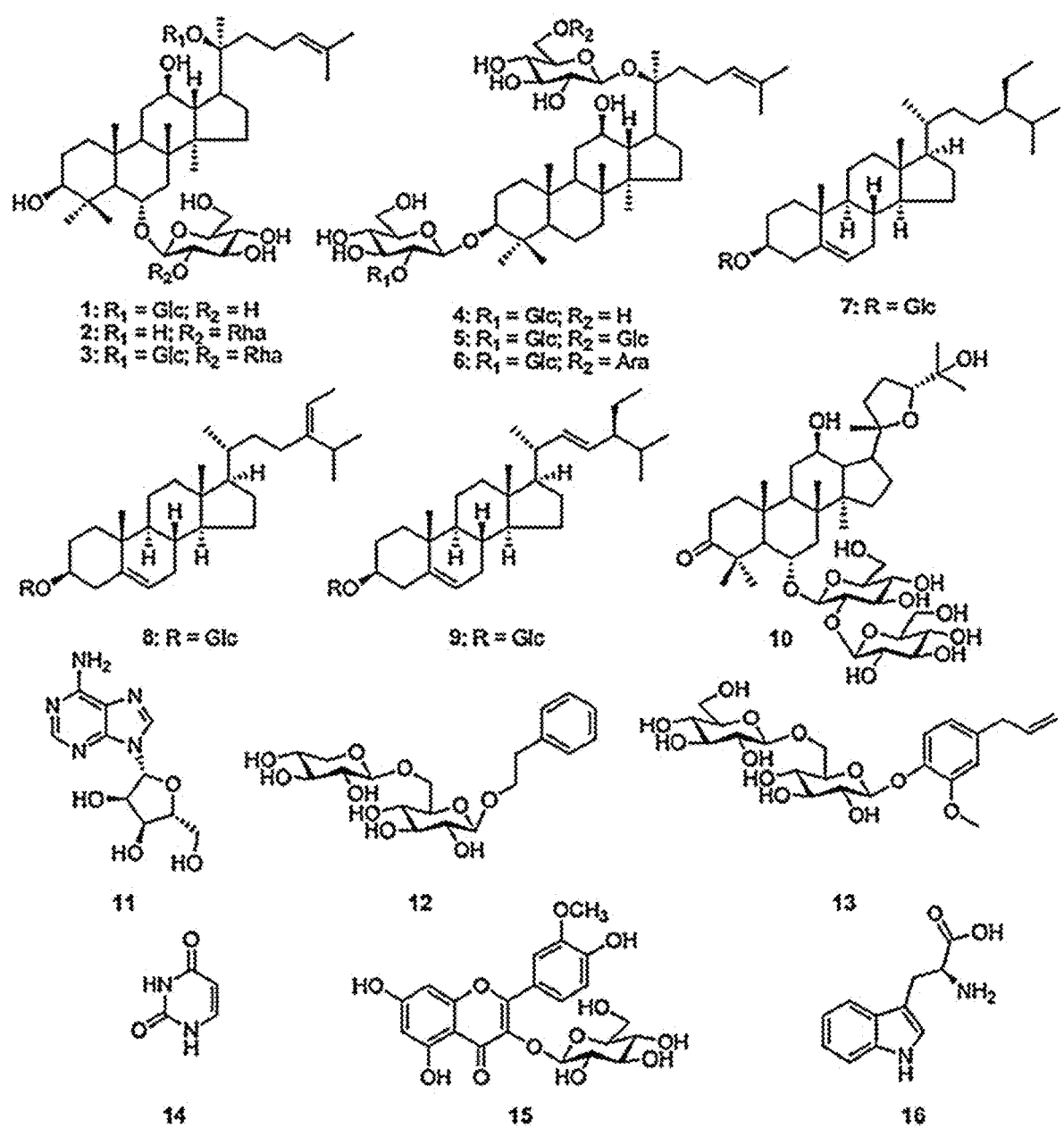
FIG. 2 is a diagram illustrating the chemical structures of 16 compounds fractionated from ginseng seed extract.
Figure 3:
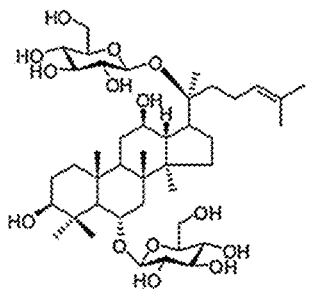
FIG. 3 is a diagram illustrating the spectroscopic evidence and structures of compounds 1 to 6 corresponding to the previously known ginsenosides among the compounds fractionated from ginseng seed extract.
Figure 3:
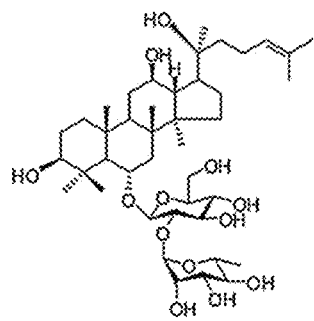
Figure 3:
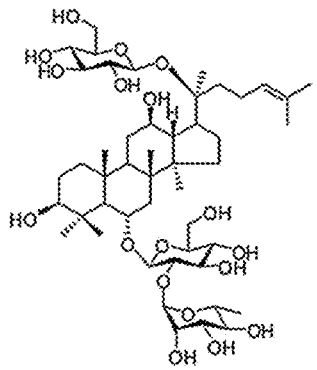
Figure 3:
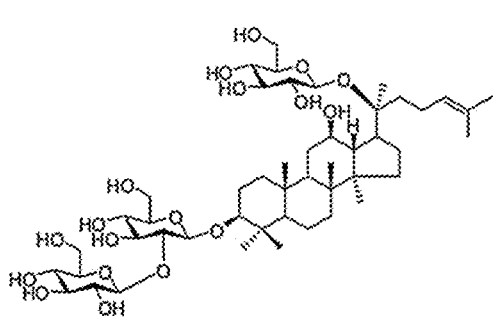
Figure 3:
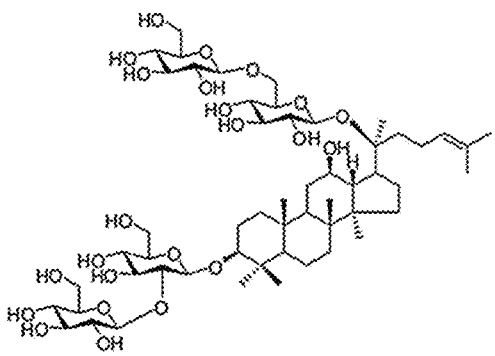
Figure 3:
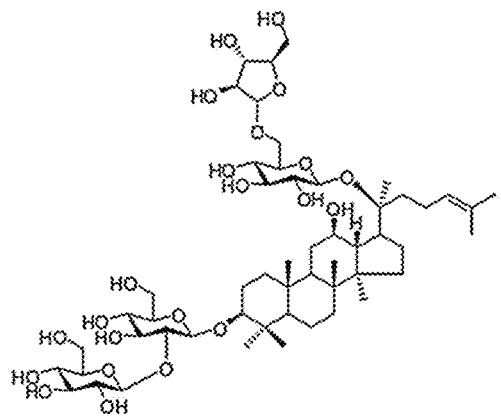
Figure 4:
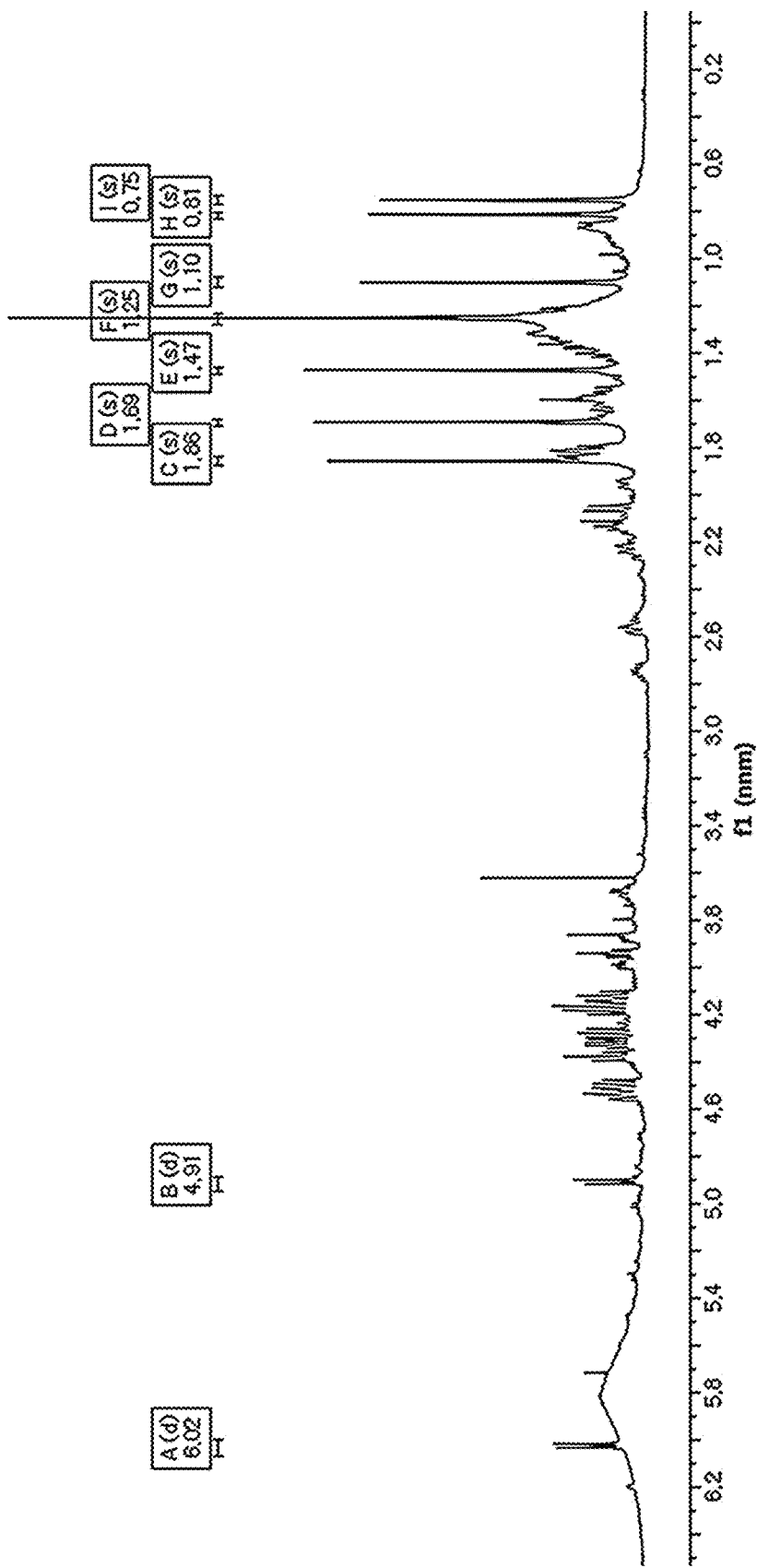
FIG. 4 is a diagram illustrating a $^1$H-NMR spectrum of compound 10 corresponding to the novel ginsenoside of the present disclosure among the compounds fractionated from ginseng seed extract.
Figure 5:
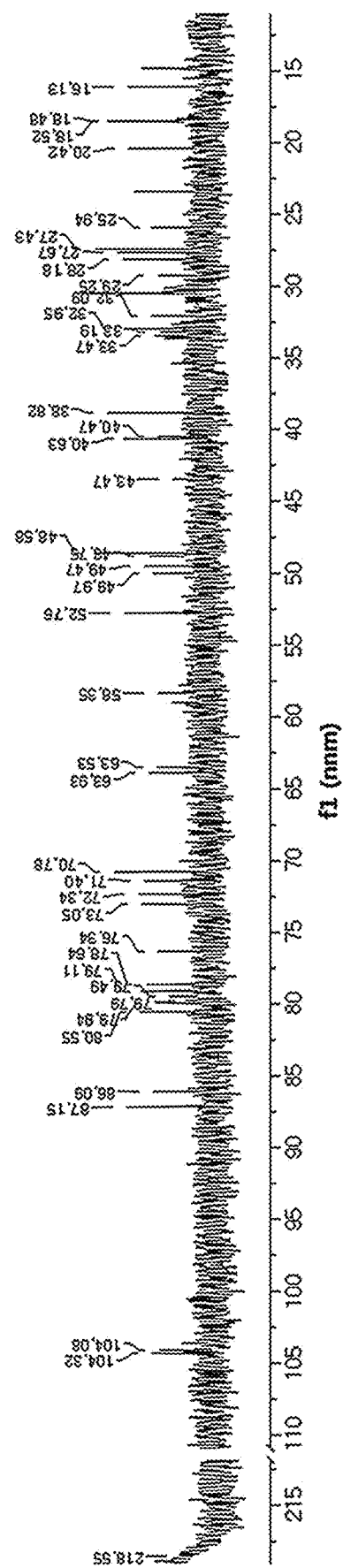
FIG. 5 is a diagram illustrating a $^{13}$C-NMR spectrum of compound 10 corresponding to the novel ginsenoside of the present disclosure among the compounds fractionated from ginseng seed extract.
Figure 6:
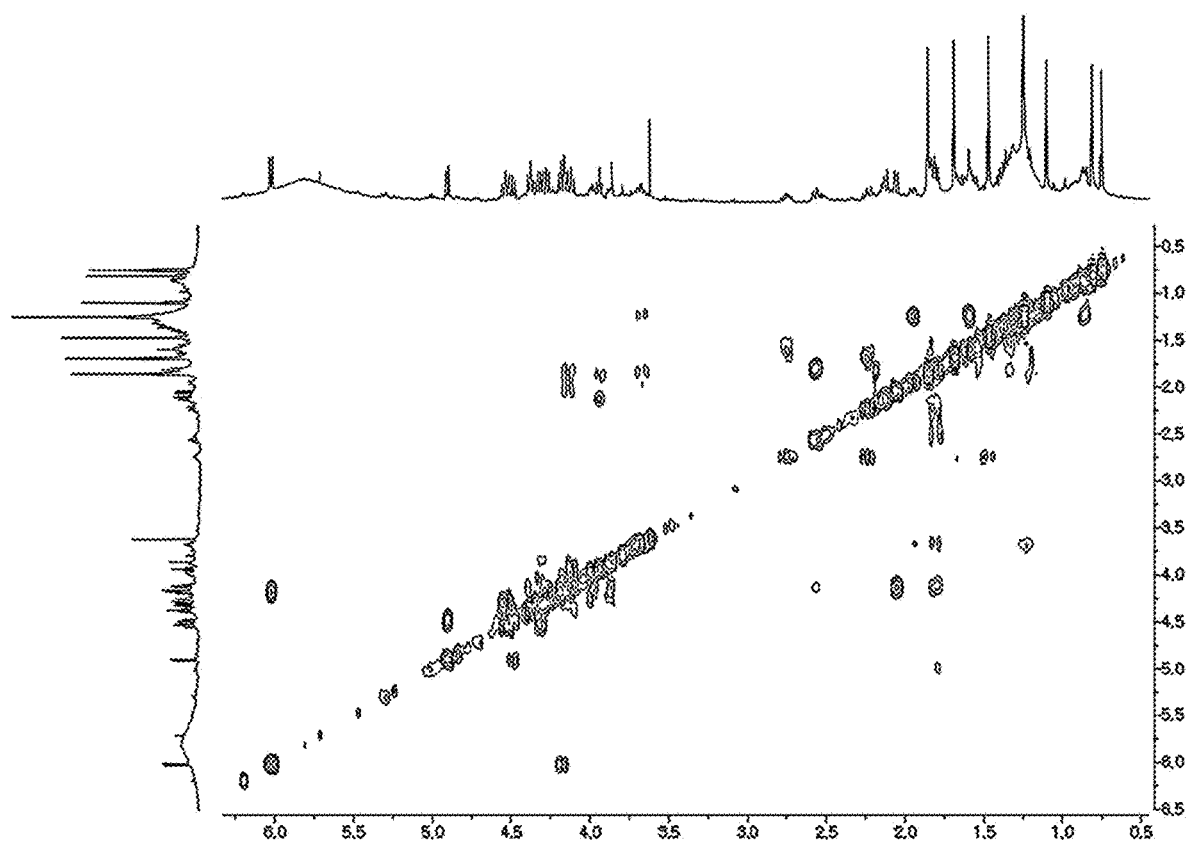
FIG. 6 is a diagram illustrating a COSY spectrum of compound 10 corresponding to the novel ginsenoside of the present disclosure among the compounds fractionated from ginseng seed extract.
Figure 7:
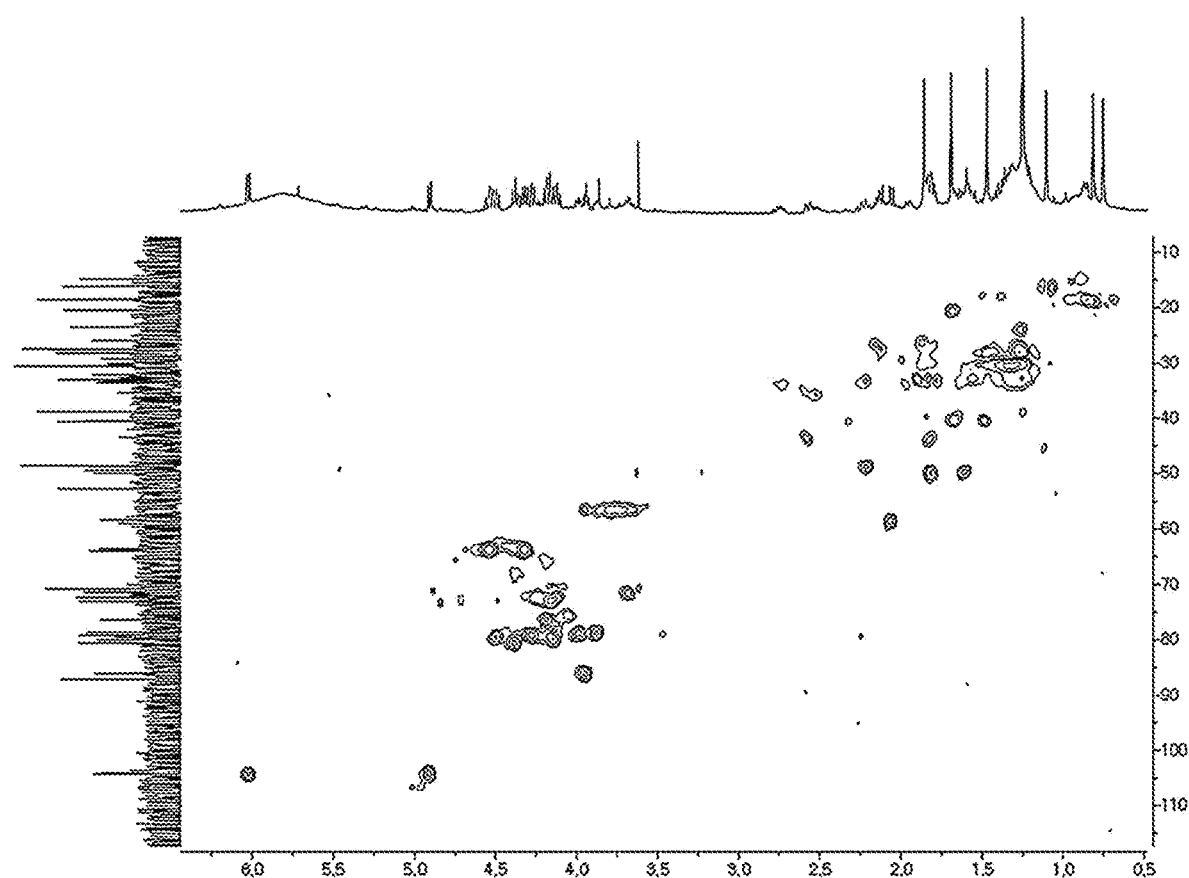
FIG. 7 is a diagram illustrating an HSQC spectrum of compound 10 corresponding to the novel ginsenoside of the present disclosure among the compounds fractionated from ginseng seed extract.
Figure 8:
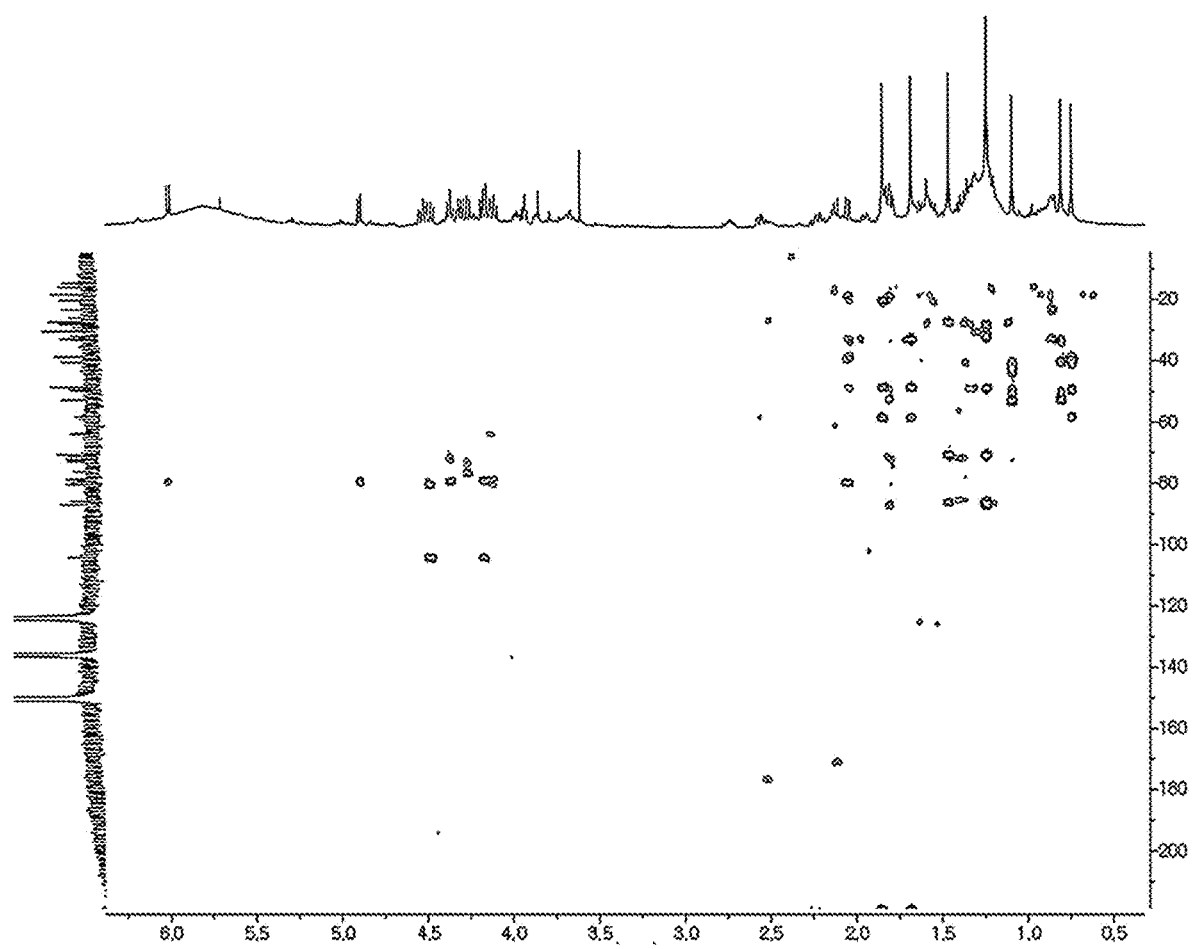
FIG. 8 is a diagram illustrating an HMBC spectrum of compound 10 corresponding to the novel ginsenoside of the present disclosure among the compounds fractionated from ginseng seed extract.
Figure 9:
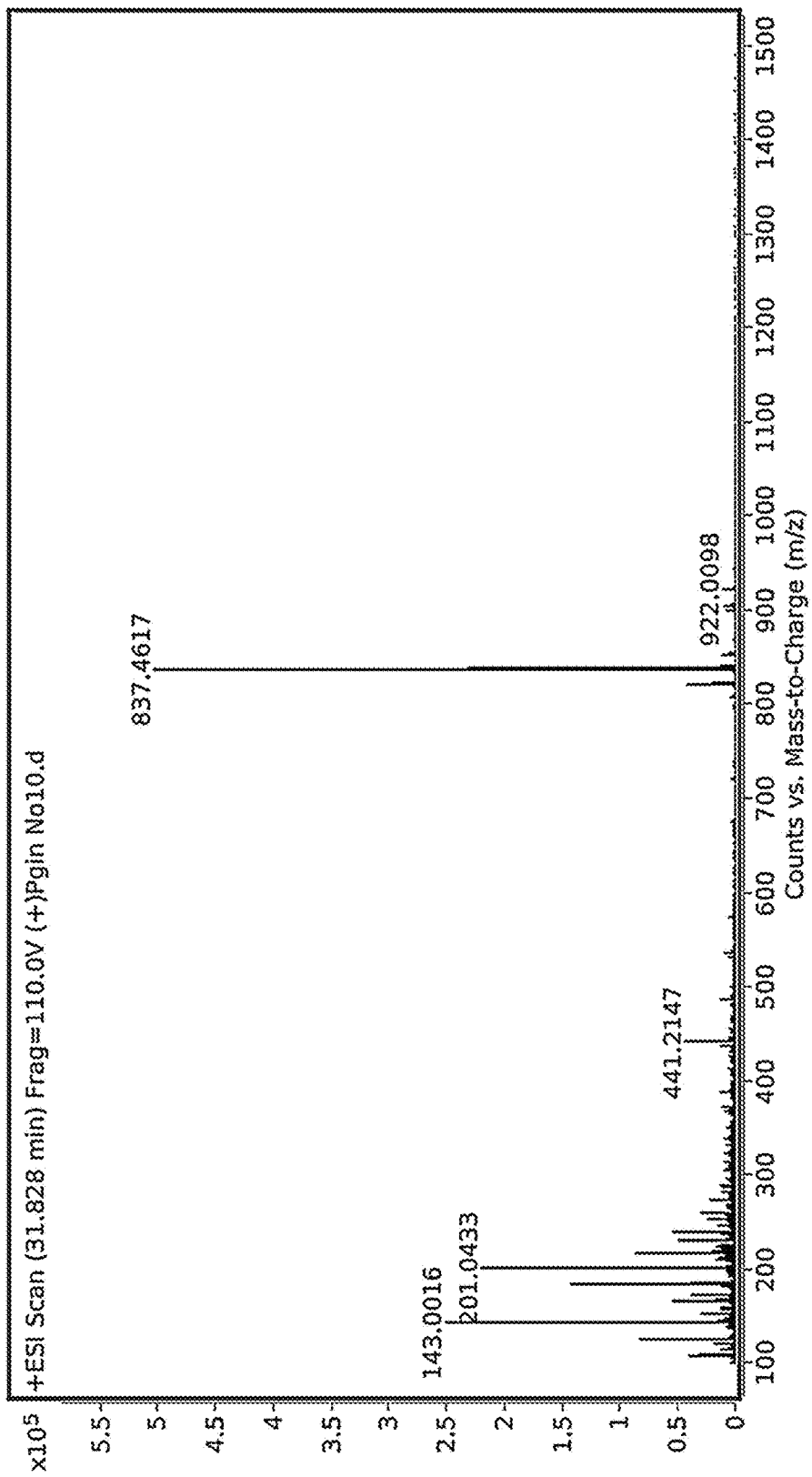
FIG. 9 is a diagram illustrating an MS spectrum of compound 10 corresponding to the novel ginsenoside of the present disclosure among the compounds fractionated from ginseng seed extract.
Figure 10:
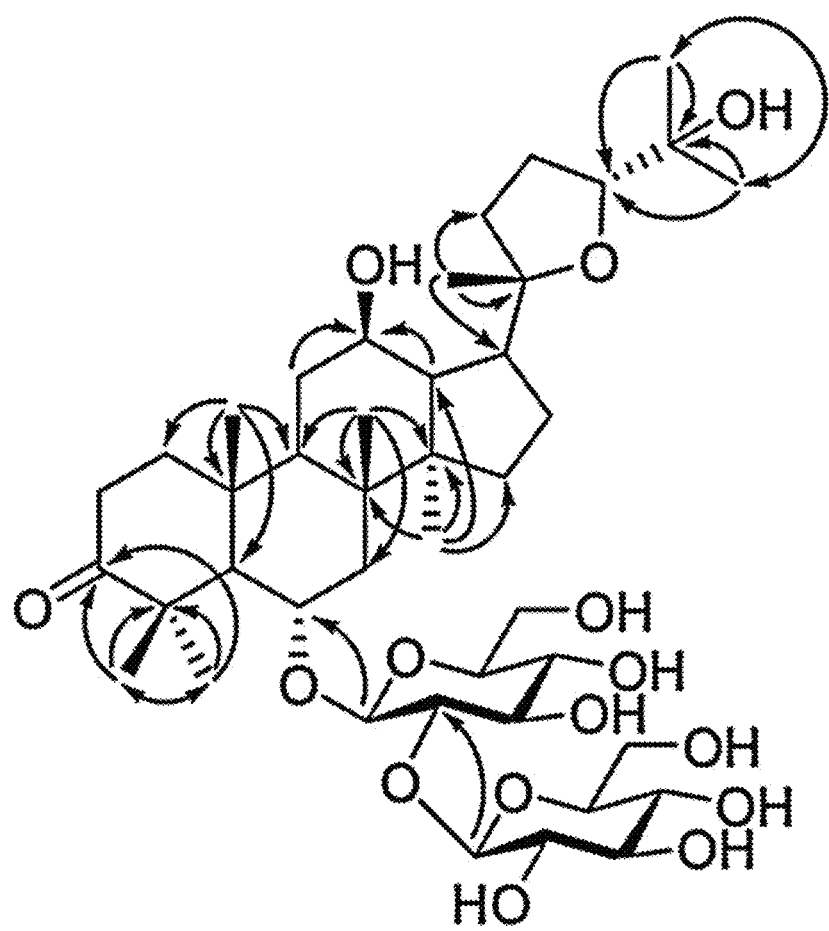
FIG. 10 is a diagram illustrating the core HMBC correlation of compound 10 corresponding to the novel ginsenoside of the present disclosure among the compounds fractionated from ginseng seed extract.

An isolation process of a novel ginsenoside according to an embodiment of the present disclosure corresponding to compound 10 above is shown in FIG. 1. The chemical structures of the 16 compounds are shown in FIG. 2, and spectroscopic evidence and chemical structures of the conventionally known ginsenoside compounds 1-6 among the above compounds are separately shown in FIG. 3.

Compound 10 was isolated as a white amorphous powder showing the molecular formula of $C_{42}H_{70}O_{15}$ based on the sodiated pseudomolecular ion peak at m/z 837.4617 [(M+Na)$^+$ calcd. 837.4612] in the cationic ESI-Q-TOF-MS (Electrospray Ionization-Quadrupole-Time-of-flight mass spectrometry) spectrum. The $^1$H NMR spectrum of the compound 10 contained 8 methyl resonances in [$\delta_H$1.86 (3H, s, H-28), 1.69 (3H, s, H-29), 1.47 (3H, s, H-27), 1.25 (6H, s, H-21, 26), 1.10 (3H, s, H-18), 0.81 (3H, s, H-30), 0.75 (3H, s, H-19)]. In addition, two pairs of signals corresponding to the anomeric protons and carbon atoms at the two sugar residues were detected at $\delta_H$6.02 (1H, d, J=7.8, H-2")/$\delta_C$104.08 (C-1') and $_H$4.91 (1H, d, J=7.7, H-1')/$\delta_C$104.32 (C-1"). $^{13}$CNMR and heteronuclear single quantum correlation (HSQC) spectra revealed 42 carbon signals. Apart from the two sugar residues above, the aglycone of compound 10 had eight methylenes, four methines, three oxygen-containing methines [$\delta_C$79.79 (C-6), 71.40 (C-12) and 86.09 (C-24)], five quaternary carbon atoms, two oxygenated quaternary carbon atoms [$\delta_C$87.15 (C-20) and 70.78 (C-25)], and eight methyl groups and carbonyl carbon [$\delta_C$218.85 (C-3)]. As a result of thorough interpretation of $^1$H and $^{13}$CNMR data, the aglycone of compound 10 was found to be superimposed on pseudoginsengenin R1 [(20S, 24R)-dammar-3-one-20,24-epoxy-6a,123,25-triol])]. The absolute configuration of C-20 in compound 10 was deduced from S to chemical shift of C-21 ($\delta_C$27.67), and the 24R configuration was determined by chemical shift of C-24 ($\delta_C$86.09) as previously disclosed. Both sugar units were turned out to be β-D-glucopyranosyl residues from the coupling constants of the anomeric protons at 1H NMR spectra and 12 carbon resonances, together with acid hydrolysis data and gas chromatography (GC) analysis results. A glycoside linkage was determined by heteronuclear multiple bond correlation (HMBC) which showed cross peaks at $\delta_H$6.02 (H-1")/$\delta_C$79.49 (C-2') and $\delta_H$4.91 (H-1')/$\delta_C$79.79 (C-6), and it was demonstrated that 2-O-(β-D-glucopyranosyl)-β-D-glucopyranosyl residues were linked to C-6 of aglycone at pseudoginsengenin R1. Each of the analytical spectra of the compound 10 and the core HBMC correlation are shown in FIGS. 4 to 10.

In the above analysis results, it was determined that the chemical structure of compound 10 was (20S,24R)-6-O-β-D-glucopyranosyl(1→2)-β-D-glucopyranoside-dammar-3-one-20,24-epoxy-6a,12b,25-triol, and named pseudoginsenoside RT8 (PG-RT$_8$).

Among the ginsenosides isolated from the ginseng seed extract, ginsenoside Rg1 (compound 1), ginsenoside Rg2 (compound 2) and ginsenoside Re (compound 3), which are PPT (ProtoPanaxTriol) based ginsenosides, comprise three hydroxyl groups in the ginsenoside backbone. Ginsenoside Rd (compound 4), ginsenoside Rb1 (compound 5), and ginsenoside Rb2 (compound 6), which are PPD (ProtoPanax Diol) based ginsenosides, comprise two hydroxyl groups in the ginsenoside backbone. On the other hand, compound 10, which is a newly isolated and identified ginsenoside in the present disclosure, has a PPT-based backbone, but the terminal hydroxyl group of the backbone is ketone, and there is a structural difference in that the linear chain of ginsenoside is cyclized with a furan ring.

In the present disclosure, the molecular formula of the newly isolated and identified compound 10 was $C_{92}H_{70}O_{15}$, ESI-Q-TOF-MS, m/z was 837.4617 [M+Na]$^+$, and $^1$H, $^{13}$C-NMR spectra are shown in the following table.

TABLE 1

| Position | 13C-NMR | 1H-NMR |
|---|---|---|
| 1 | 40.63 | 1.67 (1H, H-1a)$^a$, 1.49 (1H, H-1b)$^a$ |
| 2 | 33.62 | 2.23(1H, H-2a)$^a$, 1.49 (1H, H-2b)$^a$ |
| 3 | 218.85 | — |
| 4 | 48.58 | — |
| 5 | 58.35 | 2.06 (3H, d, j = 10.6 Hz, H-5) |
| 6 | 79.79 | 4.15 (1H, H-6)$^a$ |
| 7 | 43.47 | 2.57 (1H, H-7a)$^a$, 1.82 (1H, H7b)$^a$ |
| 8 | 40.47 | — |
| 9 | 49.47 | 1.60 (1H, H-9)$^a$ |
| 10 | 38.82 | — |
| 11 | 33.47 | 2.22 (3H, H-11a)$^a$, 1.32 (1H, H-11b)$^a$ |
| 12 | 71.40 | 3.68 (1H, td, j = 10.6, 4.5 Hz, H-12) |
| 13 | 49.97 | 1.81 (1H, H-13)$^a$ |
| 14 | 52.76 | — |
| 15 | 33.19 | 1.64 (1H, H-15a)$^a$, 1.26 (1H, H-15b)$^a$ |
| 16 | 25.94 | 2.17 (1H, H-16a)$^a$, 1.87 (1H, H-16b)$^a$ |
| 17 | 48.75 | 2.21 (3H, H-17)$^a$ |
| 18 | 16.13 | 1.10 (3H, s, H-18) |
| 19 | 18.48 | 0.75 (3H, s, H-19) |
| 20 | 87.15 | — |
| 21 | 27.67 | 1.25 (3H, s, H-21) |
| 22 | 32.09 | 1.60 (1H, H-22a)$^a$, 1.37 (1H, H-22b)$^a$ |
| 23 | 29.25 | 1.82 (1H, H-23a)$^a$, 1.25 (1H, H-23b)$^a$ |
| 24 | 86.09 | 3.94 (1H, t, j = 7.5 Hz, H-24) |
| 25 | 70.78 | — |
| 26 | 27.43 | 1.25 (3H, s, H-26) |
| 27 | 28.18 | 1.45 (3H, s, H-27) |
| 28 | 32.95 | 1.86 (3H, s, H-28) |
| 29 | 20.42 | 1.69 (3H, s, H-29) |
| 30 | 18.52 | 0.81 (3H, s, H-30) |

$^a$peak was overlapped

TABLE 2

| Position | 13C-NMR | 1H-NMR |
|---|---|---|
| 6-O-Glc | | |
| 1' | 104.08 | 4.91 (1H, d, j = 7.7 Hz, H-1') |
| 2' | 79.49 | 4.48 (1H, m, H-2') |
| 3' | 80.55 | 4.38 (1H, m, H-3') |
| 4' | 73.05 | 4.16 (1H, m, H-4') |

TABLE 2-continued

| Position | 13C-NMR | 1H-NMR |
|---|---|---|
| 5' | 79.94 | 4.15 (1H, m, H-5') |
| 6' | 63.53 | 4.54 (1H, m, H-6'a), 4.32 (1H, m, H-6'b) |
| 2'-O-Glc | | |
| 1" | 104.32 | 6.02 (1H, d, j = 7.8 Hz, H-1") |
| 2" | 76.34 | 4.18 (1H, m, H-2") |
| 3" | 78.64 | 3.99 (1H, m, H-3") |
| 4" | 72.34 | 4.12 (1H, m, H-4") |
| 5" | 79.11 | 4.27 (1H, m, H-5") |
| 6" | 63.93 | 4.54 (1H, m, H-6"a), 4.32 (1H, m, H-6"b) |

[Test Example 1] Comparison of Exercise Ability Enhancing Efficacy 1

Exercising by moving muscles requires a large amount of energy (adenosine triphosphate; ATP), and ATP is synthesized and supplied mainly through the mitochondrial electron transport system. Accordingly, in order to improve exercise ability (endurance), the amount of mitochondria in the muscle should be increased and thus fatty acid oxidation should be promoted. Thus, the following experiments were performed to determine whether ginseng seed-derived ginsenoside GS #10 according to one embodiment of the present disclosure can activate mitochondria and fat metabolism in myocytes.

Ginseng seed-derived ginsenosides were administered to mouse-derived myocyte lines (C2C12; ATCC) to observe changes in mitochondrial amount and fatty acid oxidation in myocytes.

The mouse-derived myocyte lines (C2C12; ATCC) were cultured using Dulbecco's Modified Eagle's Medium (DMEM; Sigma) containing 5% fetal bovine serum (Hyclone) and 1% penicillin/streptomycin (Sigma). The cells were induced to be 100% confluent for differentiation into myocytes and then differentiated using a DMEM medium containing 2% horse serum (Hyclone) and 1% penicillin/streptomycin (Sigma). Medium was changed daily, with differentiation for a total of a week. After a week of differentiation, the C2C12 myoblasts, which were in the form of general fibroblasts, change into elongated shapes, making it easy to confirm the degree of myocyte differentiation with naked eye.

Figure 11:
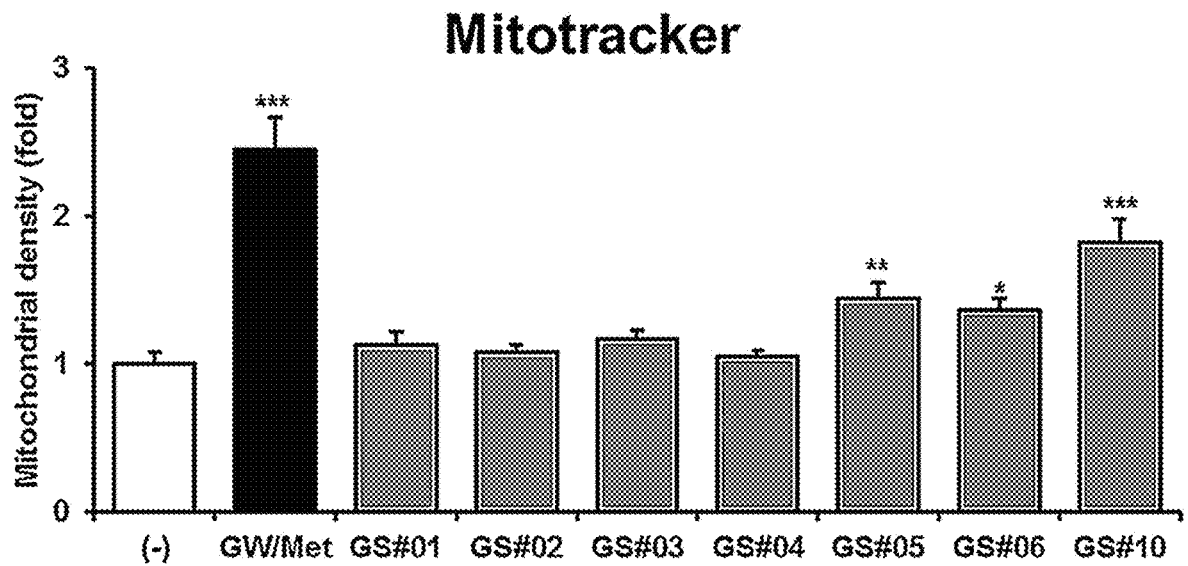
FIG. 11 is a diagram showing a comparison of the mitochondrial production ability in myocytes of GS #10 corresponding to the novel ginsenoside of the present disclosure isolated from a ginseng seed extract and ginsenosides GS #01-GS #06, which are comparative examples of the present disclosure. (* $P<0.001$ vs. (−),  $P<0.01$ vs. (−), * $P<0.05$ vs. (−))
Figure 12:
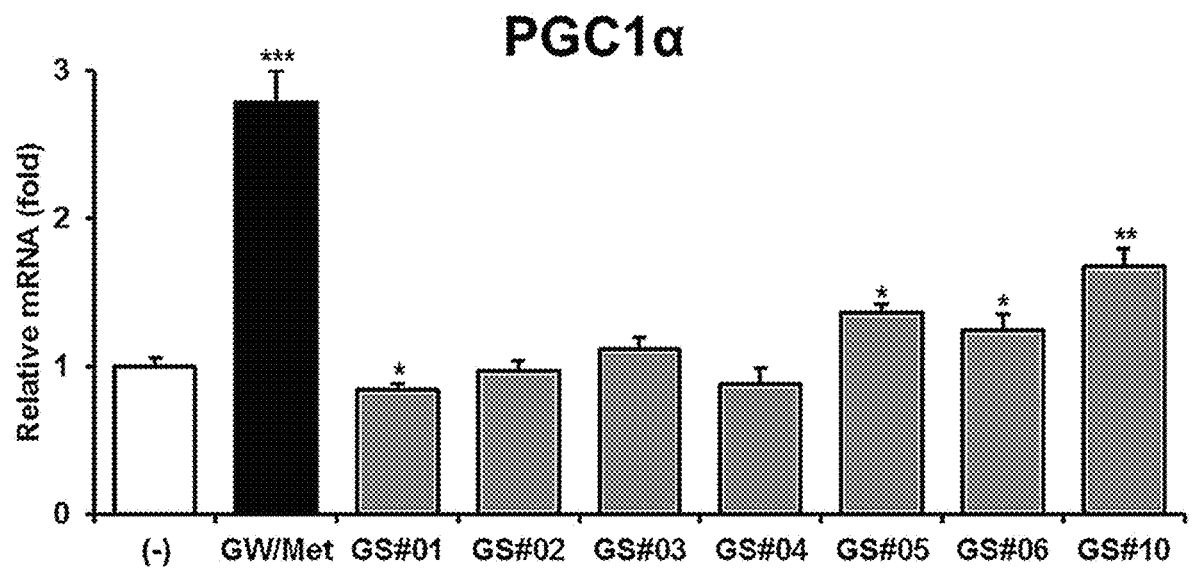
FIG. 12 is a diagram showing a comparison of the expression levels of mitochondrial gene (PGC1α) in myocytes of GS #10 corresponding to the novel ginsenoside of the present disclosure isolated from a ginseng seed extract and ginsenosides GS #01-GS #06, which are comparative examples of the present disclosure. (* $P<0.001$ vs. (−),  $P<0.01$ vs. (−), * $P<0.05$ vs. (−))
Figure 13:
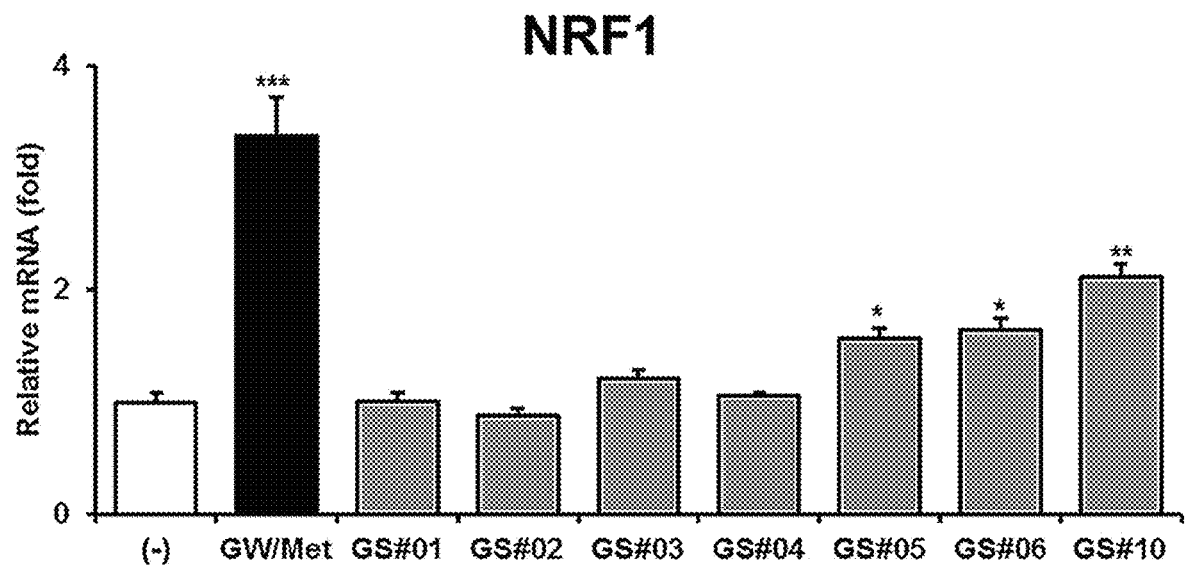
FIG. 13 is a diagram showing a comparison of the expression levels of mitochondrial gene (NRF1) in myocytes of GS #10 corresponding to the novel ginsenoside of the present disclosure isolated from a ginseng seed extract and ginsenosides GS #01-GS #06, which are comparative examples of the present disclosure. (* $P<0.001$ vs. (−),  $P<0.01$ vs. (−), * $P<0.05$ vs. (−))
Figure 14:
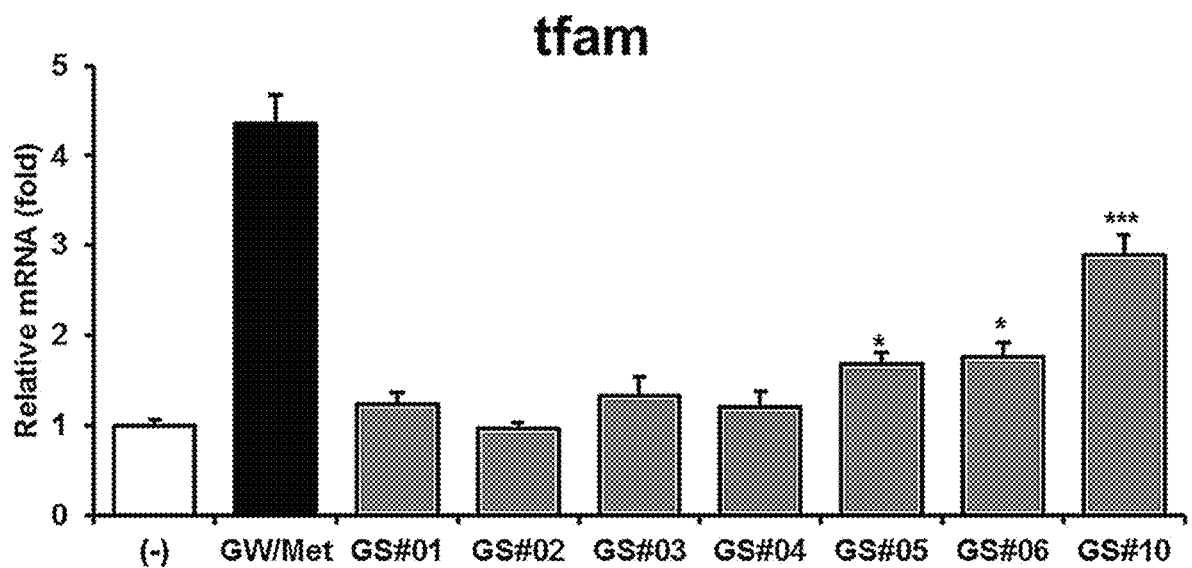
FIG. 14 is a diagram showing a comparison of the expression levels of mitochondrial gene (tfam) in myocytes of GS #10 corresponding to the novel ginsenoside of the present disclosure isolated from a ginseng seed extract and ginsenosides GS #01-GS #06, which are comparative examples of the present disclosure. (* $P<0.001$ vs. (−),  $P<0.01$ vs. (−), * $P<0.05$ vs. (−))

After treating the differentiated myocytes with the novel ginsenoside GS #10 of one embodiment of the present disclosure and the other ginsenosides GS #01-GS #06 isolated from the existing ginseng seed extract at a concentration of 20 pg/ml for 24 hours, respectively, the amount of mitochondria in myocytes was observed by staining with a Mitotracker Green™ (Invitrogen) reagent. mRNA expression levels of mitochondrial marker genes were measured using Q-PCR. As positive controls, a combination of GW501516 and Metformin (GW/Met; treated at 10 μM each), which are candidates for exercise mimetics and are known to improve exercise ability by activating PPARδ (Peroxisome proliferator-activated receptor delta) and AMPK (AMP-activated protein kinase), respectively, was used. The mitochondrial number measured as a result of the test is shown in FIG. 11, and the mitochondrial marker gene expression levels are shown in FIGS. 12 to 14. In addition, it was confirmed whether fatty acid oxidation could be increased in myocytes due to the actually increased mitochondria, and the result is shown in FIG. 15.

Figure 15:
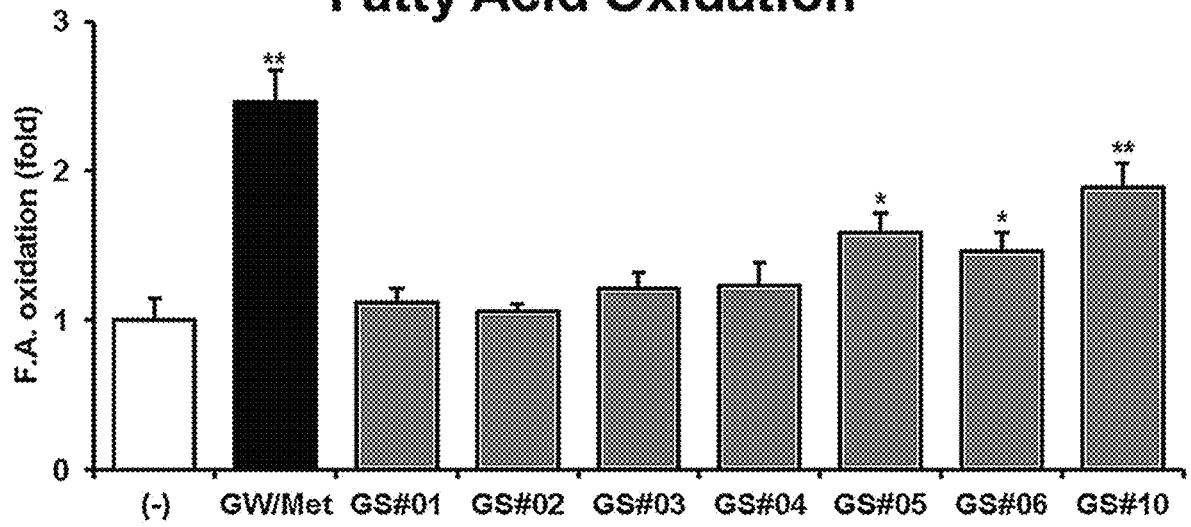
FIG. 15 is a diagram showing a comparison of the fatty acid oxidation promoting ability of GS #10 corresponding to the novel ginsenoside of the present disclosure isolated from a ginseng seed extract and ginsenosides GS #01-GS #06, which are comparative examples of the present disclosure. (** $P<0.01$ vs. (−), * $P<0.05$ vs. (−))

As a result, the mitochondrial biosynthesis ability of the novel ginsenoside GS #10 of one embodiment of the present disclosure was the most excellent (FIGS. 11 to 14), and accordingly, the fatty acid oxidation in myocytes was also increased the most (FIG. 15).

[Test Example 2] Comparison of Exercise Ability Enhancing Efficacy 2

Figure 16:
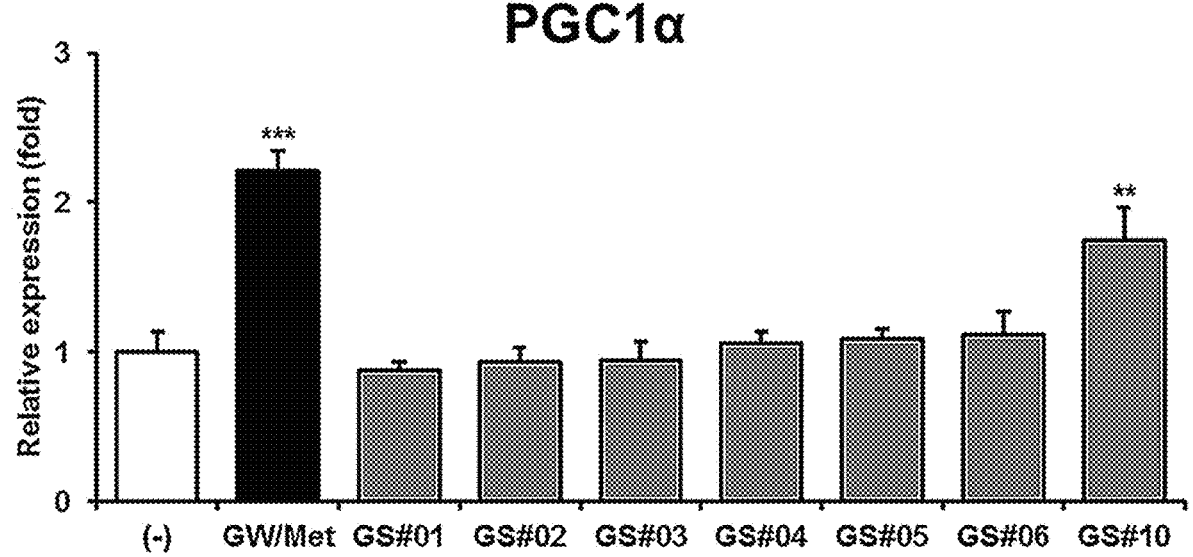
FIG. 16 is a diagram showing a comparison of the expression levels of mitochondrial gene (PGC1α) measured in a treadmill experiment of GS #10 corresponding to the novel ginsenoside of the present disclosure isolated from a ginseng seed extract and ginsenosides GS #01-GS #06, which are comparative examples of the present disclosure. (* $P<0.001$ vs. (−),  $P<0.01$ vs. (−))
Figure 17:
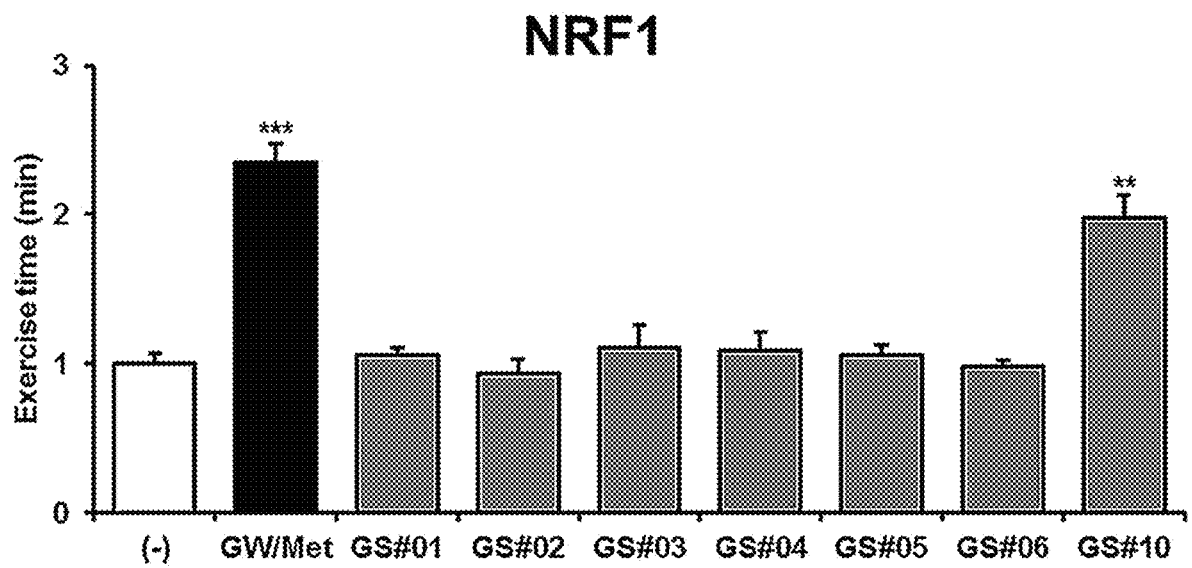
FIG. 17 is a diagram showing a comparison of the expression levels of mitochondrial gene (NRF1) measured in a treadmill experiment of GS #10 corresponding to the novel ginsenoside of the present disclosure isolated from a ginseng seed extract and ginsenosides GS #01-GS #06, which are comparative examples of the present disclosure. (* $P<0.001$ vs. (−),  $P<0.01$ vs. (−))
Figure 18:
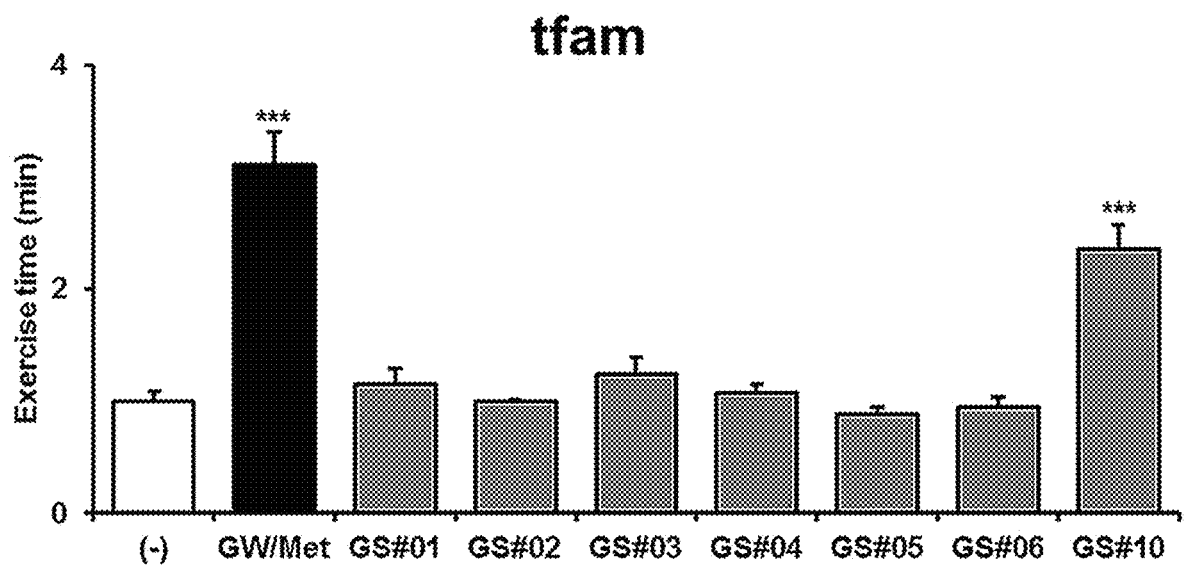
FIG. 18 is a diagram showing a comparison of the expression levels of mitochondrial gene (tfam) measured in a treadmill experiment of GS #10 corresponding to the novel ginsenoside of the present disclosure isolated from a ginseng seed extract and ginsenosides GS #01-GS #06, which are comparative examples of the present disclosure. (* $P<0.001$ vs. (−),  $P<0.01$ vs. (−))

The following experiment was performed to confirm whether the exercise ability improving effect due to the increased mitochondrial production and lipid metabolism promotion of the ginseng seed-derived novel ginsenoside (GS #10) confirmed in Test Example 1 above was also shown at the actual individual level. 20 mg/kg each of the novel ginsenoside GS #10 of one embodiment of the present disclosure and the other ginsenosides GS #01-GS #06 isolated from the existing ginseng seed extract was orally administered to 39-week-old female Sprague-Dawley (SD) mice, and 10 mg/kg each thereof was orally administered to the control group GW/Met for 6 weeks. In order to improve the treadmill adaptability during the six-week experiment, mice were placed on the treadmill every two weeks to familiarize them with the use of the treadmill. After six weeks of administration, mice were placed on a treadmill to run on the treadmill. The exercise time was until the mice were exhausted and pushed down from the treadmill, and the mice which finished the exercise was immediately extracted of muscle tissue and plasma by necropsy. The expression of mitochondria-related genes was observed in muscle tissues, and lactic acid concentration, a marker of muscle fatigue, was measured in the blood. The expression patterns of mitochondrial marker genes in muscle are shown in FIGS. 16 to 18, and exercise time and plasma lactate in blood are shown in FIGS. 19 and 20.

As a result, although the other ginsenosides GS #05 and GS #06 isolated from the existing ginseng seed extract showed a slight mitochondria increasing efficacy in cell experiments, this result did not appear to the experimental animals. Thus, the actual mitochondrial activity and the exercise ability improving efficacy were confirmed to be insignificant (FIGS. 16 to 20).

On the other hand, it was confirmed that the expression of mitochondrial marker gene was significantly increased in the muscles of the mice ingested with the novel ginsenoside GS #10 of one embodiment of the present disclosure as in the experiment using the myocyte line in Test Example 1. This means that the mitochondrial number actually increased in the muscles of mice ingested with the novel ginsenoside GS #10 of one embodiment of the present disclosure, thereby more activating fat consumption in the muscle and inducing more ATP production (FIGS. 16-18).

Figure 19:
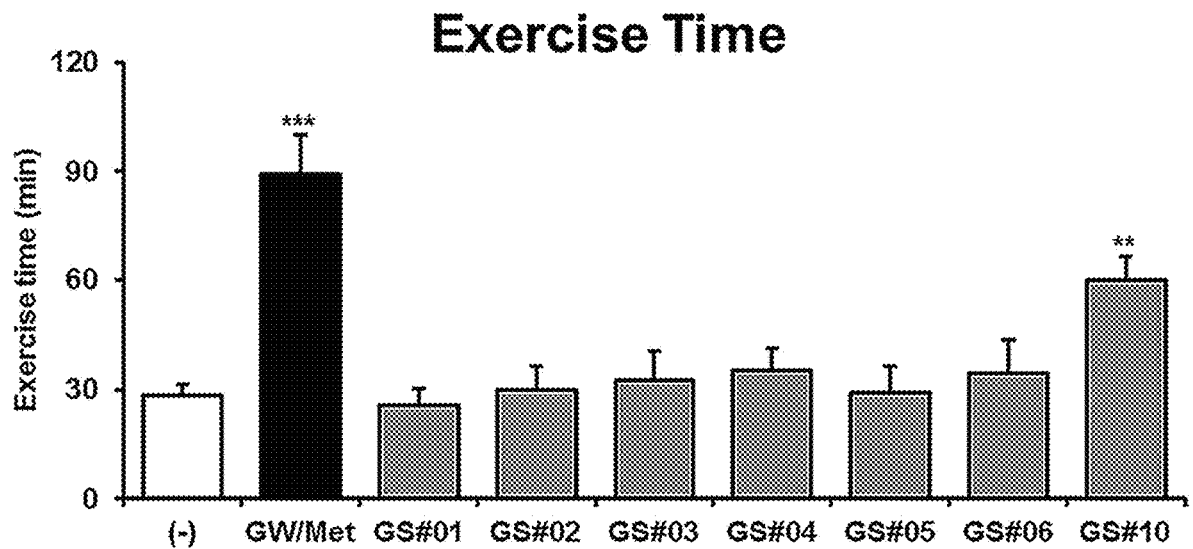
FIG. 19 is a diagram showing a comparison of a time duration of exercise (exercise time) measured in a treadmill experiment of GS #10 corresponding to the novel ginsenoside of the present disclosure isolated from a ginseng seed extract and ginsenosides GS #01-GS #06, which are comparative examples of the present disclosure. (* $P<0.001$ vs. (−),  $P<0.01$ vs. (−))
Figure 20:
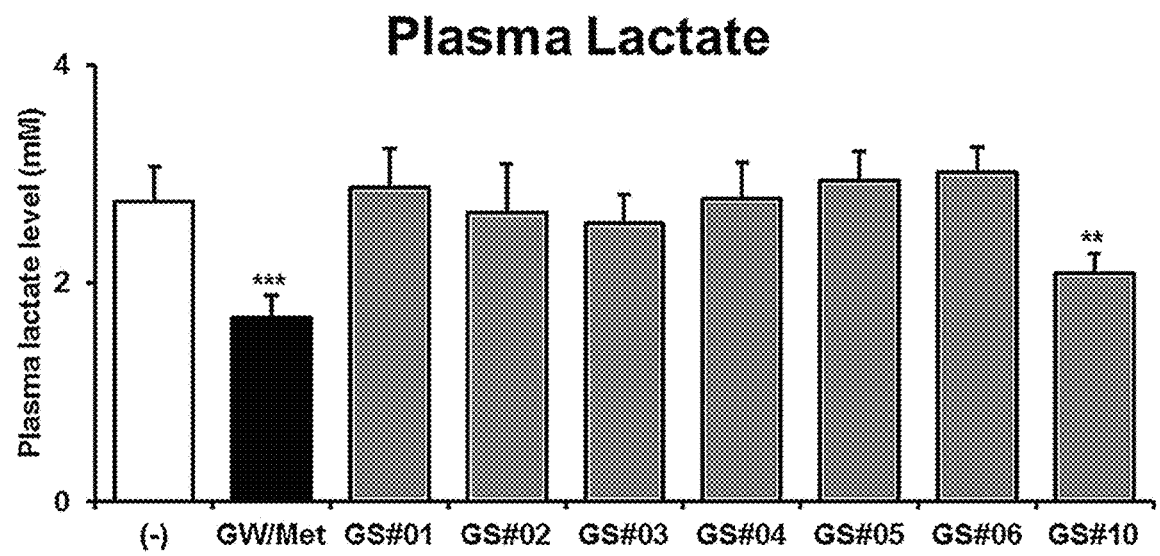
FIG. 20 is a diagram showing a comparison of the decrease levels of a lactic acid concentration (plasma lactate) measured in a treadmill experiment of GS #10 corresponding to the novel ginsenoside of the present disclosure isolated from a ginseng seed extract and ginsenosides GS #01-GS #06, which are comparative examples of the present disclosure. (* $P<0.001$ vs. (−),  $P<0.01$ vs. (−))
Figure 21:
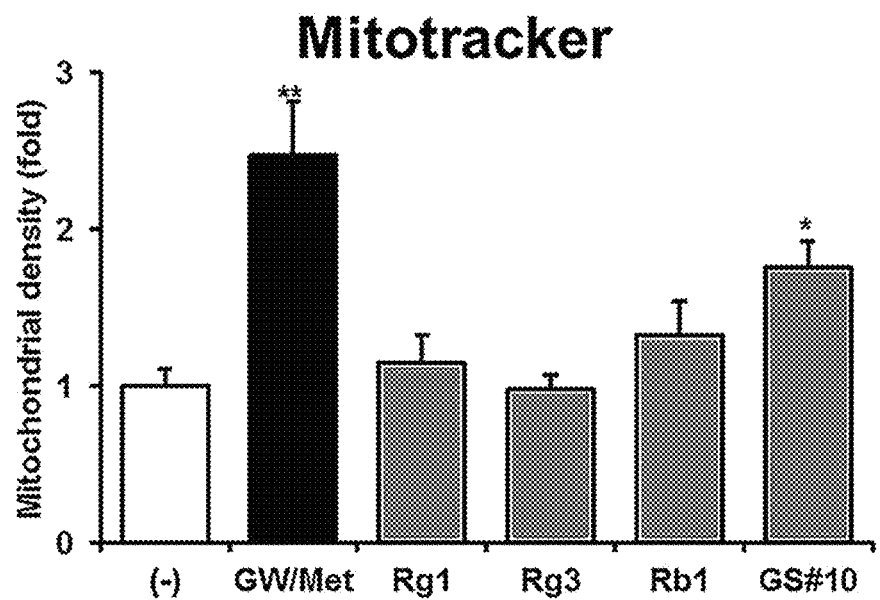
FIG. 21 is a diagram showing a comparison of the mitochondrial production ability in myocytes of ginsenosides Rg1, Rg3 and Rb1 of the red ginseng index components and GS #10 corresponding to the novel ginsenoside of the present disclosure. (* $P<0.001$ vs. (−),  $P<0.01$ vs. (−), * $P<0.05$ vs. (−))
Figure 22:
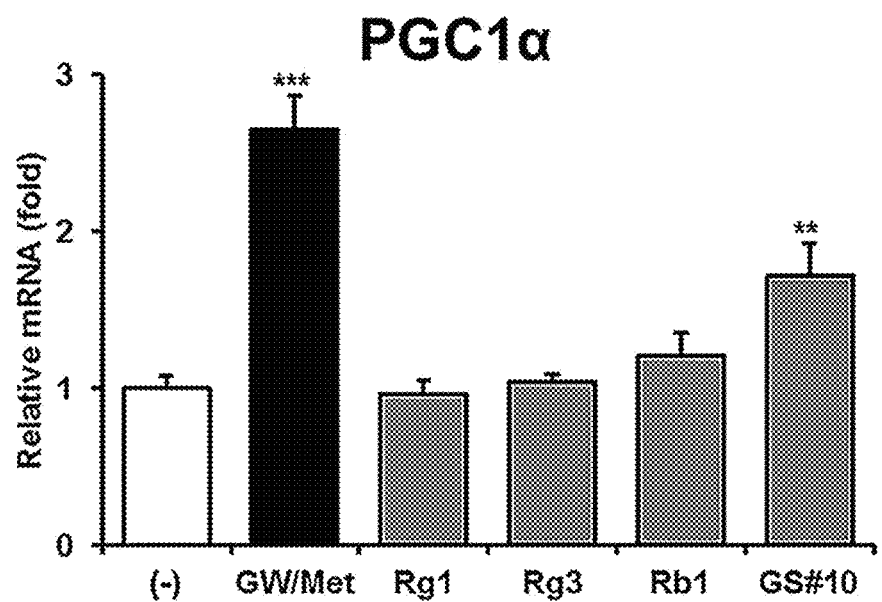
FIG. 22 is a diagram showing a comparison of the expression levels of mitochondrial gene (PGC1α) in myocytes of ginsenosides Rg1, Rg3 and Rb1 of the red ginseng index components and GS #10 corresponding to the novel ginsenoside of the present disclosure. (* $P<0.001$ vs. (−),  $P<0.01$ vs. (−), * $P<0.05$ vs. (−))
Figure 23:
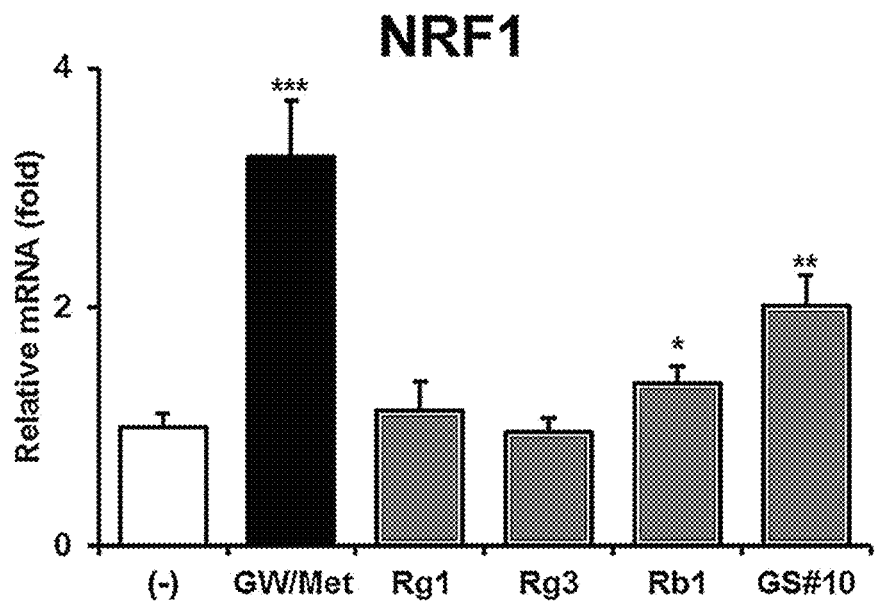
FIG. 23 is a diagram showing a comparison of the expression levels of mitochondrial gene (NRF1) in myocytes of ginsenosides Rg1, Rg3 and Rb1 of the red ginseng index components and GS #10 corresponding to the novel ginsenoside of the present disclosure. (* $P<0.001$ vs. (−),  $P<0.01$ vs. (−), * $P<0.05$ vs. (−))
Figure 24:
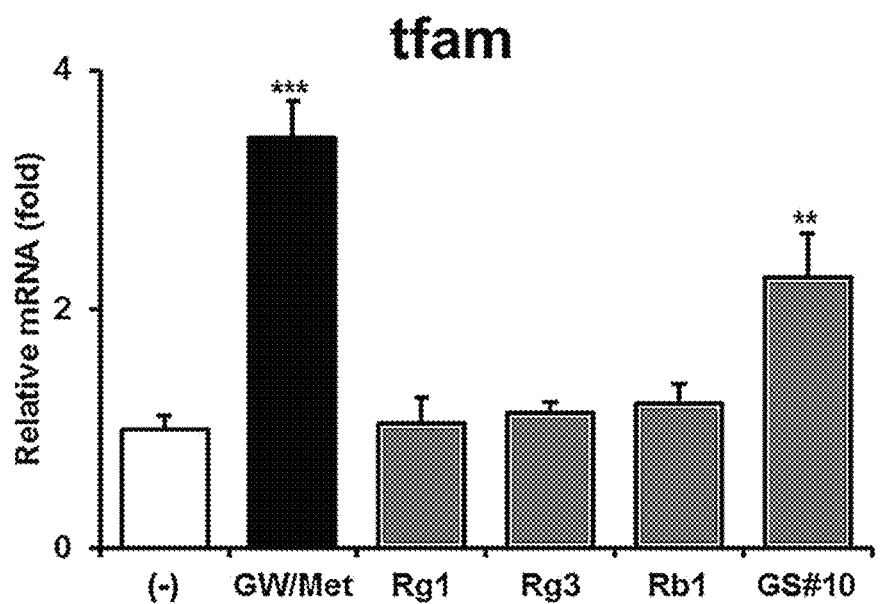
FIG. 24 is a diagram showing a comparison of the expression levels of mitochondrial gene (tfam) in myocytes of ginsenosides Rg1, Rg3 and Rb1 of the red ginseng index components and GS #10 corresponding to the novel ginsenoside of the present disclosure. (* $P<0.001$ vs. (−),  $P<0.01$ vs. (−), * $P<0.05$ vs. (−))

In addition, the novel ginsenoside GS #10 of one embodiment of the present disclosure doubled the exercise time and showed the lowest pattern of a lactic acid concentration, a muscle fatigue marker, as compared to the other ginsenosides GS #01-GS #06 isolated from the existing ginseng seed extract (FIGS. 19 and 20). It is determined that the novel ginsenoside GS #10 of one embodiment of the present disclosure generates a lot of energy through the regulation of mitochondrial activity even at the actual individual level, which leads to an improvement in exercise ability.

[Test Example 3] Comparison of Exercise Ability Enhancing Efficacy 3

The exercise ability enhancing efficacy of the novel ginsenoside GS #10 of one embodiment of the present disclosure was compared with ginsenosides Rg1, Rg3 and Rb1 (purchased from Sigma) of the red ginseng index components as a comparative example of the present disclosure. At this time, the chemical structure of ginsenoside Rg3, which is a comparative example of the present disclosure, is as follows.

[Formula 2]

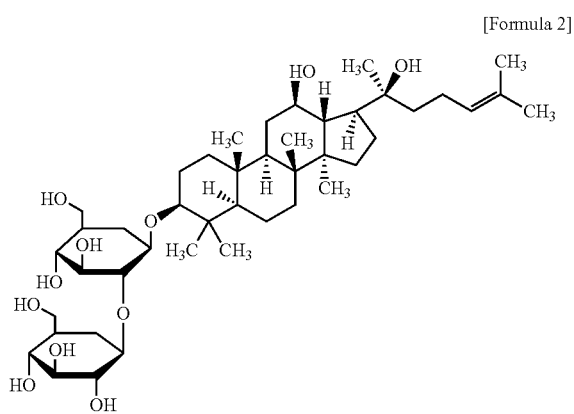

The experiments were performed in the same manner as in Test Examples 1 and 2 above, respectively.

First, the C2C12 myocytes differentiated in the same manner as in Test Example 1 above were treated with ginsenosides Rg1, Rg3, and Rb1, which are comparative examples of the present disclosure, and the novel ginsenoside GS #10 of one embodiment of the present disclosure, respectively, and then mitochondria and marker genes were observed (FIGS. 21 to 25). In addition, in the same manner as in Test Example 2 above, after administration of 20 mg/kg each of ginsenosides Rg1, Rg3, Rb1, which are comparative examples of the present disclosure, and the novel ginsenoside GS #10 of one embodiment of the present disclosure for 6 weeks to the mice, the exercise ability was observed.

Figure 25:
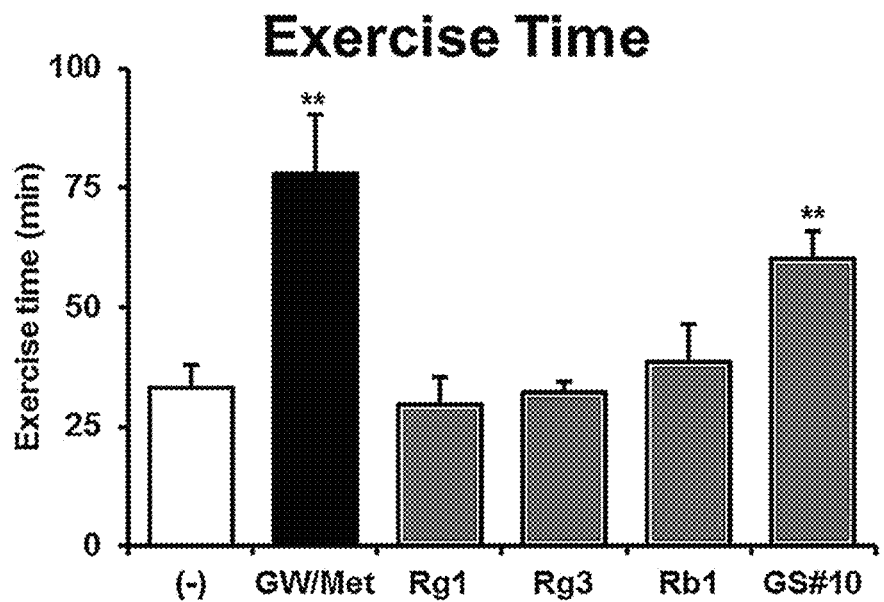
FIG. 25 is a diagram showing a comparison of a time duration of exercise (exercise time) measured in a treadmill experiment of ginsenosides Rg1, Rg3 and Rb1 of the red ginseng index components and GS #10 corresponding to the novel ginsenoside of the present disclosure. (* $P<0.001$ vs. (−),  $P<0.01$ vs. (−))
Figure 26:
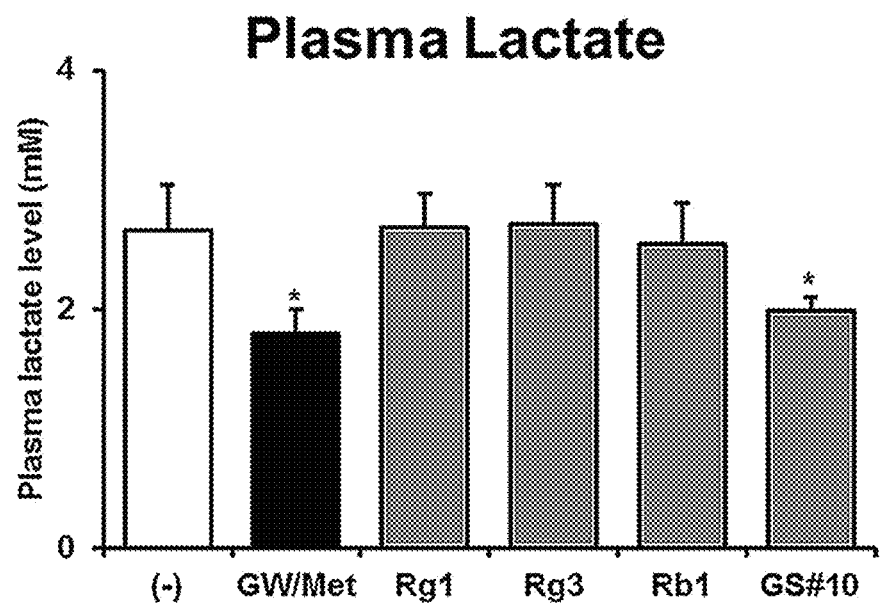
FIG. 26 is a diagram showing a comparison of the decrease levels of a lactic acid concentration (plasma lactate) measured in a treadmill experiment of ginsenosides Rg1, Rg3 and Rb1 of the red ginseng index components and GS #10 corresponding to the novel ginsenoside of the present disclosure. (* $P<0.001$ vs. (−),  $P<0.01$ vs. (−))

As a result, as shown in FIGS. 21 to 24, ginsenosides Rg1, Rg3, and Rb1, which are comparative examples of the present disclosure, did not increase mitochondria production, whereas only novel ginsenoside GS #10 of one embodiment of the present disclosure showed mitochondria increasing efficacy. In addition, as shown in FIGS. 25 and 26, even in the animal experiments, only novel ginsenoside GS #10 of one embodiment of the present disclosure showed significant exercise ability improvement and anti-fatigue effect.

[Test Example 4] Cytotoxicity

The cell growth in the presence of novel ginsenoside GS #10 of one embodiment of the present disclosure was evaluated using Cell Counting Kit (CCK)-8 in order to exclude the possibility that ginsenosides may affect exercise ability enhancing efficacy through cytotoxic activity. The experimental method is as follows.

10 µl of a CCK-8 reagent was added to SH-SY5Y cells in culture (Dojindo, Md., USA) with reference to a 96-well plate and left at 37° C. for 2 hours, and then absorbance was measured at 450 nm. The cell viability was marked as a percentage (%) of the absolute optical density of each sample relative to the untreated sample. At this time, the concentration of the novel ginsenoside GS #10, which is an example of the present disclosure, contained in the medium in which the cells were cultured was 0.1, 1, 5, 10, 20, and 50 µM, respectively.

Figure 27:
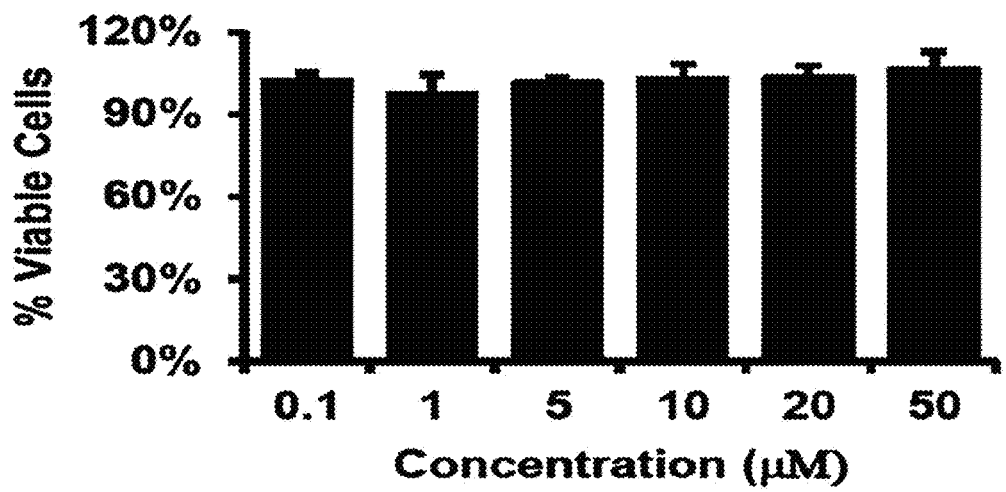
FIG. 27 is a diagram showing the cell viability (% Viable cells) of compound 10 (GS #10) corresponding to the novel ginsenoside of the present disclosure. (* $P<0.001$ vs. (−),  $P<0.01$ vs (−), * $P<0.05$ vs. (−))

As a result, as shown in FIG. 27, the novel ginsenoside GS #10, which is an example of the present disclosure, did not exhibit cytotoxicity up to 50 µM. This indicates that the novel ginsenoside, which is an example of the present disclosure, may exhibit an exercise ability enhancing effect without adversely affecting cell viability.

This suggests that the novel ginsenoside PG-RT$_8$ of one embodiment of the present disclosure has various strong exercise ability enhancing properties and has a pharmaceutical possibility as an exercise ability enhancer.

[Test Example 5] Comparison of Myoblast Growth Promoting Efficacy

Muscle cells are made from myosatellite cells present inside the muscle. They are usually in a quiescent state, and when muscle damage such as exercise is applied, they wake up and are divided to form myoblasts, and these myoblasts differentiate to form myocytes. These muscle stem cells are known to decrease in number and activity with age. In this process, the inflammatory response, especially IL-6 is involved. Therefore, it was confirmed through the following experiment whether the novel ginsenoside of the embodiment of the present disclosure can restore cell division of muscle stem cells under IL-6-mediated muscle stem cell growth inhibition conditions.

Figure 28:
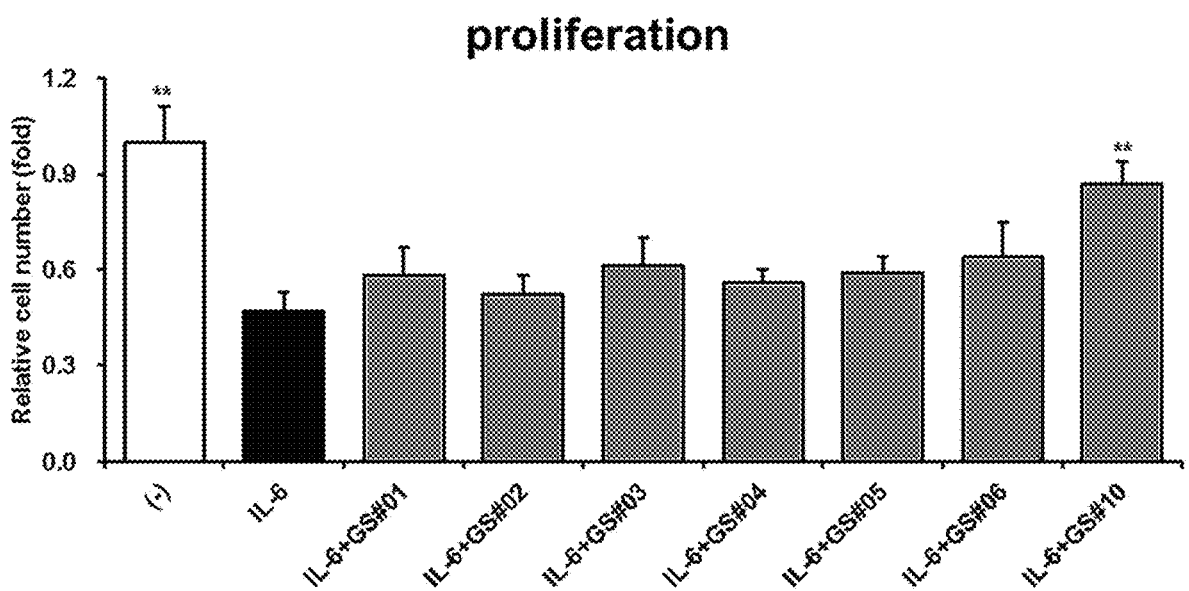
FIG. 28 is a diagram showing a comparison of the cell growth recovery levels in myoblasts induced with chronic inflammation of GS #10 corresponding to the novel ginsenoside of the present disclosure isolated from a ginseng seed extract and ginsenosides GS #01-GS #06, which are comparative examples of the present disclosure. (** $P<0.01$ vs. IL-6)

Since muscle stem cells are not available in the form of cell lines, mouse-derived muscle cell lines (C2C12, ATCC) located between muscle stem cells and myoblasts were cultured using Dulbecco's Modified Eagle's Medium (Sigma) containing 10% fetal bovine serum (Hyclone) and 1% penicillin/streptomycin (Sigma). Inflammation mediator IL-6 is produced during exercise to promote muscle energy metabolism and myoblast division/myocyte differentiation to help muscle recovery, so cells should be induced into a chronic, not acute, inflammatory state. Accordingly, in order to induce an inflammatory state due to aging, IL-6 (10 ng/ml) was treated for 4 weeks to induce myoblast aging. Myoblasts induced with chronic inflammation as such were significantly slower than normal cells in terms of cell division rate. Myoblasts of this state were treated with the novel ginsenoside GS #10 of one embodiment of the present disclosure and the other ginsenosides GS #01-GS #06 isolated from the existing ginseng seed extract at a concentration of 10 pg/ml each for 48 hours. The recovery of cell division rate was observed through the number of cells. As a result, as shown in FIG. 28, in the case of the other ginsenosides GS #01-GS #06 isolated from the existing ginseng seed extract, the recovery degree is insignificant, whereas the novel ginsenoside GS #10 of one embodiment of the present disclosure is shown to have a significant effect on the cell growth recovery of the aged myoblasts.

[Test Example 6] Comparison of Myocyte Differentiation Promoting Efficacy

Figure 29:
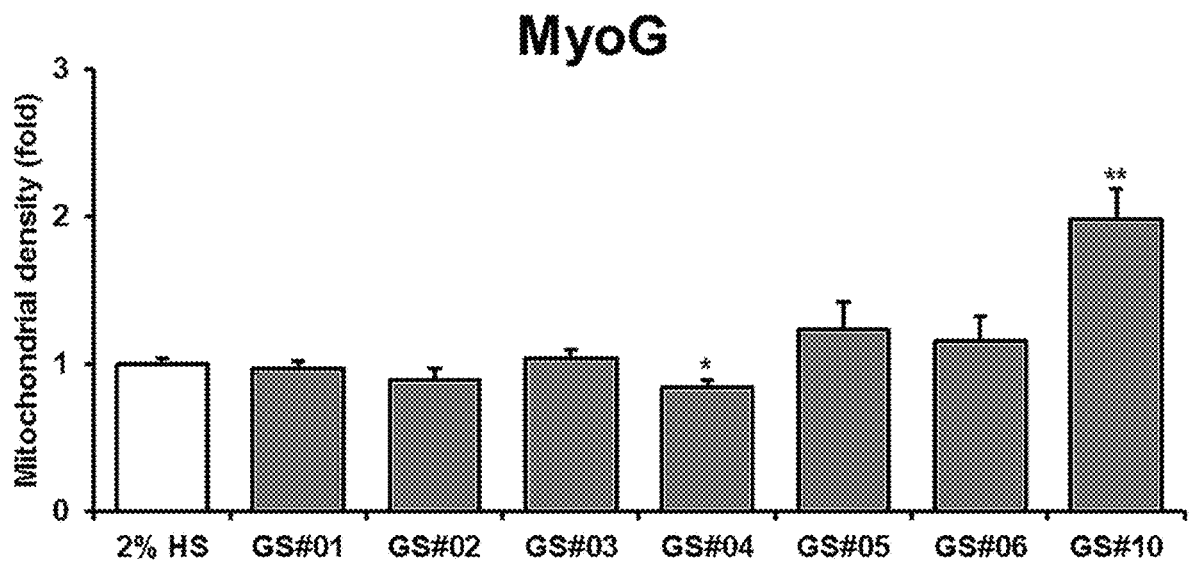
FIG. 29 is a diagram showing a comparison of the expression levels of MyoG, a transcription factor related to myocyte differentiation, as a myocyte differentiation promoting effect of GS #10 corresponding to the novel ginsenoside of the present disclosure isolated from a ginseng seed extract and ginsenosides GS #01-GS #06, which are comparative examples of the present disclosure. (** $P<0.01$ vs. 2% HS, * $P<0.05$ vs. 2% HS)
Figure 30:
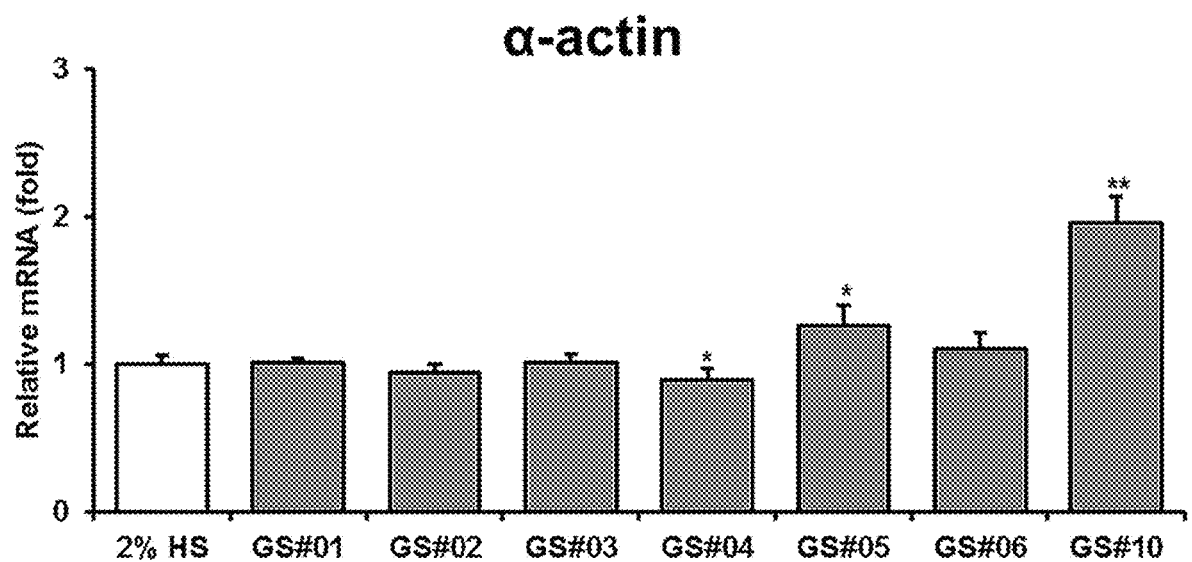
FIG. 30 is a diagram showing a comparison of the expression levels of α-actin, a muscle fiber component, as a myocyte differentiation promoting effect of GS #10 corresponding to the novel ginsenoside of the present disclosure isolated from a ginseng seed extract and ginsenosides GS #01-GS #06, which are comparative examples of the present disclosure. (** $P<0.01$ vs. 2% HS, * $P<0.05$ vs. 2% HS)
Figure 31:
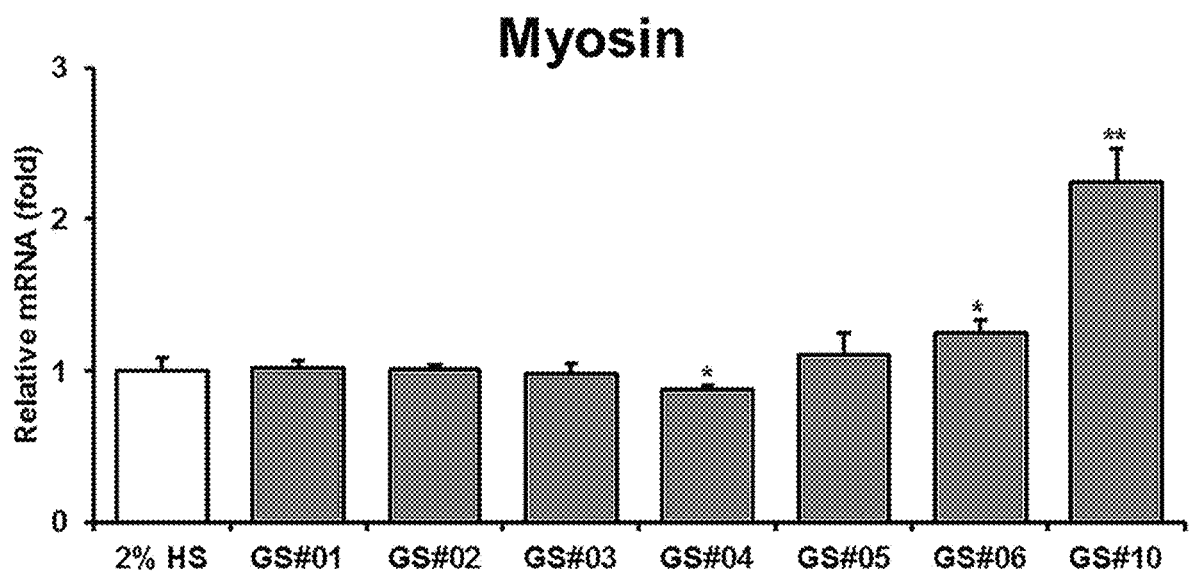
FIG. 31 is a diagram showing a comparison of the expression levels of myosin, a muscle fiber component, as a myocyte differentiation promoting effect of GS #10 corresponding to the novel ginsenoside of the present disclosure isolated from a ginseng seed extract and ginsenosides GS #01-GS #06, which are comparative examples of the present disclosure. (** $P<0.01$ vs. 2% HS, * $P<0.05$ vs. 2% HS)
Figure 32:
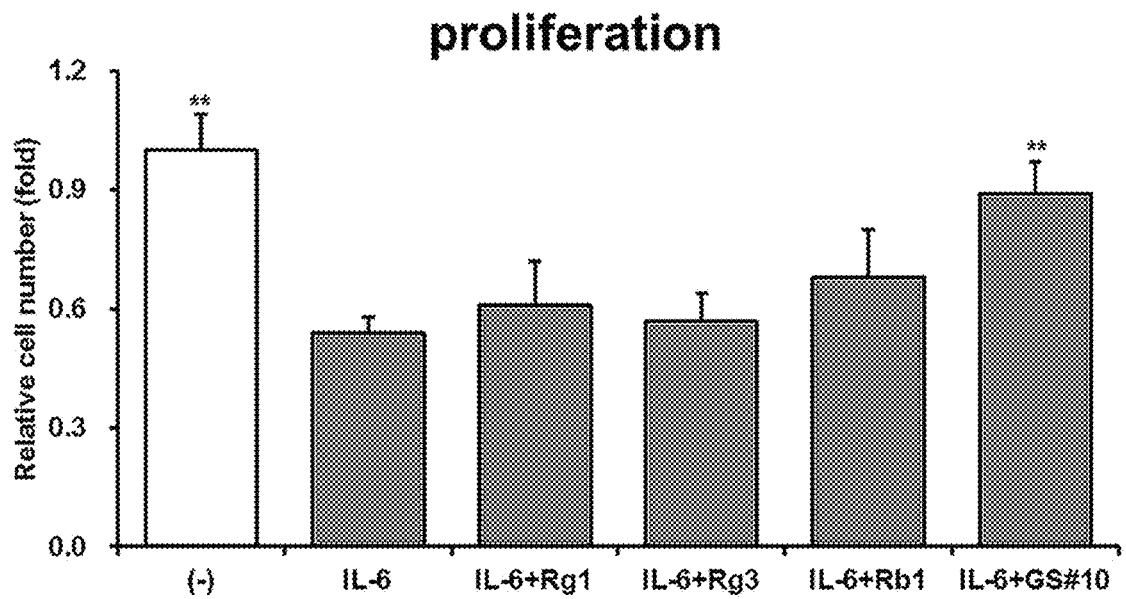
FIG. 32 is a diagram showing a comparison of the cell growth recovery levels in myoblasts induced with chronic inflammation of ginsenosides Rg1, Rg3 and Rb1 of the red ginseng index components and GS #10 corresponding to the novel ginsenoside of the present disclosure. (** $P<0.01$ vs. IL-6)
Figure 33:
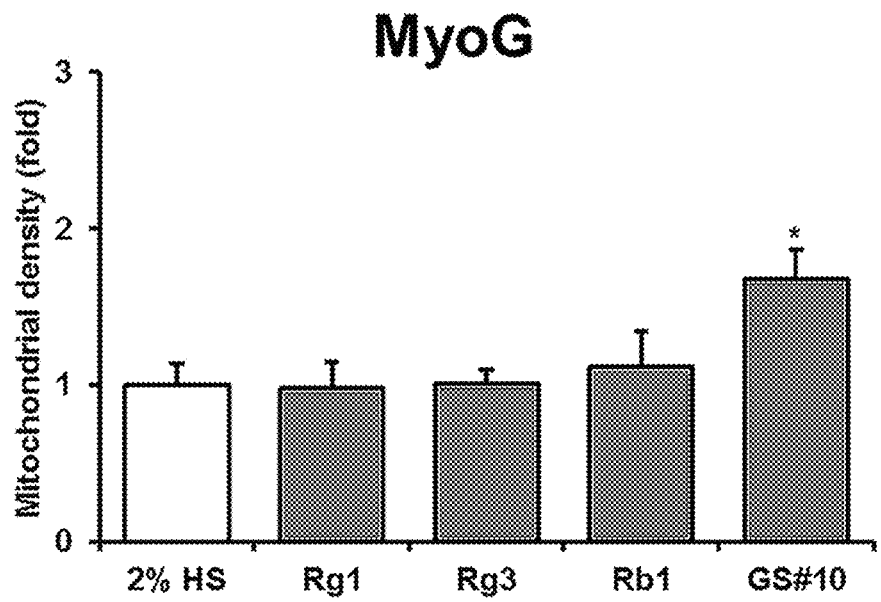
FIG. 33 is a diagram showing a comparison of the expression levels of MyoG, a transcription factor related to myocyte differentiation, as a myocyte differentiation promoting effect of ginsenosides Rg1, Rg3 and Rb1 of the red ginseng index components and GS #10 corresponding to the novel ginsenoside of the present disclosure. (** $P<0.01$ vs. 2% HS, * $P<0.05$ vs. 2% HS)
Figure 34:
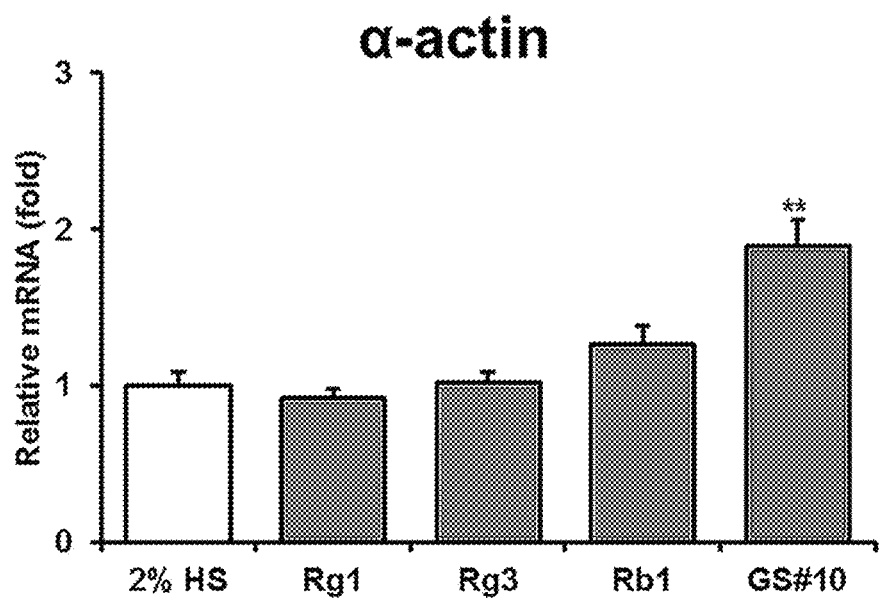
FIG. 34 is a diagram showing a comparison of the expression levels of α-actin, a muscle fiber component, as a myocyte differentiation promoting effect of ginsenosides Rg1, Rg3 and Rb1 of the red ginseng index components and GS #10 corresponding to the novel ginsenoside of the present disclosure. (** $P<0.01$ vs. 2% HS, * $P<0.05$ vs. 2% HS)
Figure 35:
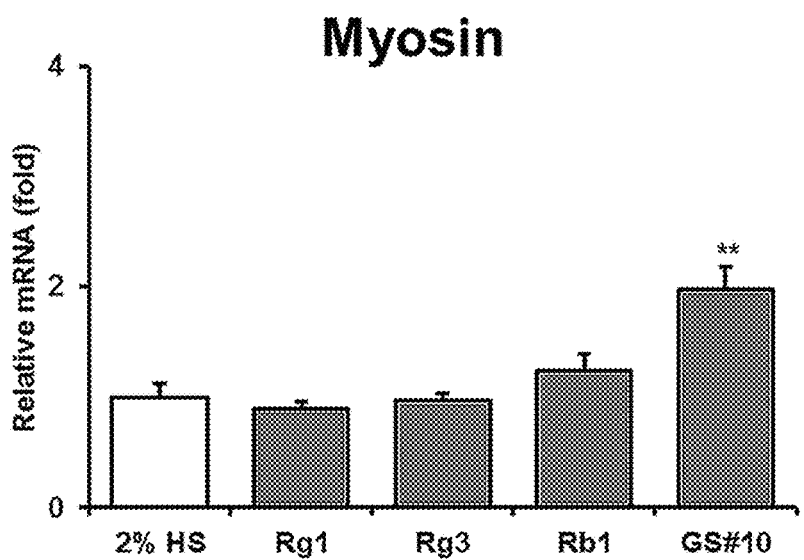
FIG. 35 is a diagram showing a comparison of the expression levels of myosin, a muscle fiber component, as a myocyte differentiation promoting effect of ginsenosides Rg1, Rg3 and Rb1 of the red ginseng index components and GS #10 corresponding to the novel ginsenoside of the present disclosure. (** $P<0.01$ vs. 2% HS, * $P<0.05$ vs. 2% HS)

As muscles decrease with age, supplementing muscle mass by differentiating myoblasts into myocytes is an essential process for maintaining muscle mass. In order to find out whether the novel ginsenoside of one embodiment of the present disclosure promotes myocyte differentiation, an experiment using a mouse-derived myocyte line (C2C12) was performed. For myocyte differentiation, cell division was induced until C2C12 myoblasts were 100% confluent to each container, and then differentiation was performed using Dulbecco's Modified Eagle's Medium (Sigma) containing 2% horse serum (Hyclone) and 1% penicillin/streptomycin (Sigma). During the differentiation period, the novel ginsenoside GS #10 of one embodiment of the present disclosure and the other ginsenosides GS #01-GS #06 isolated from the existing ginseng seed extract were treated at a concentration of 10 pg/ml, respectively. The control is differentiation medium not treated with ginsenosides. Considering that it generally takes about 7 days to differentiate myocytes, differentiation was performed only for 4 days, and cells were collected from each ginsenoside treatment group to analyze the myocyte differentiation promoting effect. After 4 days of differentiation, mRNA was extracted from each treatment group using Trizol™ reagent (Thermo Fisher Scientific), and then cDNA was synthesized using a RevertAid $1^{st}$ strand cDNA synthesis kit (Thermo Fisher Scientific). The expression levels of myoG, α-actin and myosin, which are muscle fiber marker genes, were observed using a temperature-cycling nucleic acid amplifier (CFX96 thermocycle, Bio-Rad). Among marker genes, MyoG is a transcription factor involved in myocyte differentiation, and α-actin and myosin are components of muscle fibers. As shown in FIGS. 29 to 31, among the ginseng seed-derived ginsenosides treated, only GS #10 induced a significant increase in marker gene expression. Thus, it was confirmed that the novel ginsenoside GS #10 of one embodiment of the present disclosure had a myocyte differentiation promoting effect.

[Test Example 7] Comparison of Myoblast Growth Promoting Efficacy and Myocyte Differentiation Promoting Efficacy The myoblast growth promoting efficacy and myocyte differentiation promoting efficacy of the novel ginsenoside GS #10 of one embodiment of the present disclosure were compared with those of ginsenosides Rg1, Rg3 and Rb1 (purchased from Sigma) of the red ginseng index components, which are comparative examples of the present disclosure. The experiment was performed in the same manner as in Test Examples 5 and 6. As a result, as shown in FIGS. 32 to 35, only novel ginsenoside GS #10 of one embodiment of the present disclosure showed the effects of promoting myoblast growth and myocyte differentiation.

[Test Example 8] Comparison of Anti-Fatigue Efficacy

Figure 36:
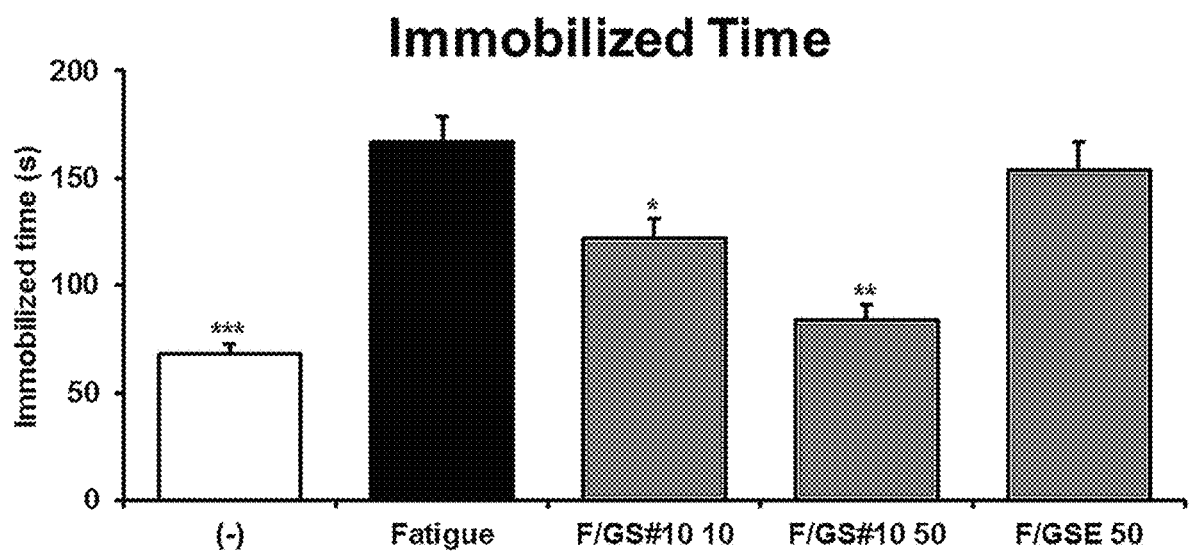
FIG. 36 is a diagram showing a comparison of FST (forced swim test) results as an anti-fatigue effect of GS #10 corresponding to the novel ginsenoside of the present disclosure isolated from a ginseng seed extract and a ginseng seed extract (GSE), which is a comparative example of the present disclosure. (* $P<0.001$ vs. Fatigue,  $P<0.01$ vs. Fatigue, * $P<0.05$ vs. Fatigue)
Figure 37:
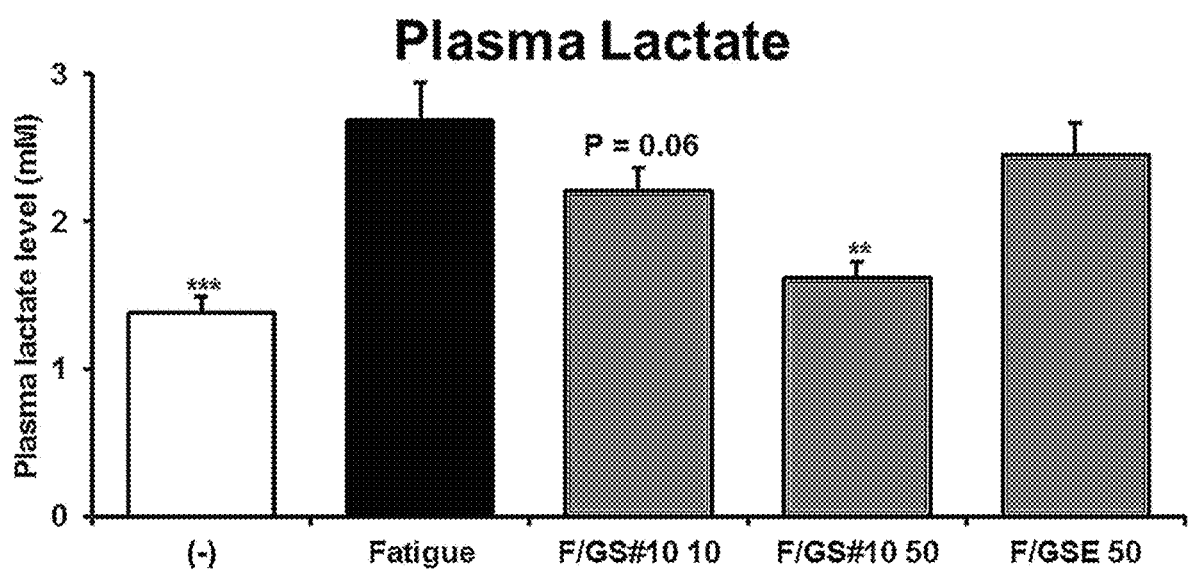
FIG. 37 is a diagram showing a comparison of the increase degree of plasma lactate in blood as a result of the FST (forced swim test) of GS #10 corresponding to the novel ginsenoside of the present disclosure isolated from a ginseng seed extract and a ginseng seed extract (GSE), which is a comparative example of the present disclosure. (* $P<0.001$ vs. Fatigue,  $P<0.01$ vs. Fatigue, * $P<0.05$ vs. Fatigue)

In Test Example 2 above, it was confirmed that the novel ginsenoside GS #10 of one embodiment of the present disclosure improved exercise ability and lowered plasma lactate in blood that is increased by exercise. In addition, the sleep deprivation-derived animal model was used to verify the anti-fatigue effect of the novel ginsenoside GS #10 of one embodiment of the present disclosure, thereby confirming the actual fatigue relief effect. Experimental methods are the same as those described in Cho et al., Biol Pharm Bull 33 (7):1128, which is incorporated herein by reference in its entirety. Balb/c mice purchased from Samtako were adapted to the age of 12 weeks and then divided into a fatigue-induced group of 32 mice and a control of 8 mice. The fatigue-induced group was divided into 4 groups again, each of 8 mice, of which is the novel ginsenoside GS #10 10 mg/kg treatment group (F/GS #10 10), 50 mg/kg treatment group (F/GS #10 50), ginseng seed extract 50 mg/kg treatment group (F/GSE #10 50), and untreated group (Fatigue). The ginseng seed extract is a comparative example of the present disclosure, and is a ginseng seed (seeds of *Panax ginseng*) methanol extract used in the isolation of ginsenoside in Example 1 described above herein. The novel ginsenoside GS #10 or ginseng seed extract was administered to each experimental group by oral administration method for 2 weeks before the experiment. Fatigue was induced in a non-sleeping manner by placing them on a rotating rotor for 24 hours and keep moving them. Then, while performing the FST (forced swim test) 6 minutes, the time during which the mice of each experiment group floated still on the water without swimming was measured to calculate fatigue. The result is shown in FIG. 36. Thereafter, the plasma lactate in blood was measured, and the degree of accumulation of the fatigue substance was observed. The result is shown in FIG. 37. As a result, the novel ginsenoside GS #10 of one embodiment of the present disclosure was shown to reduce the symptoms caused by fatigue in a concentration-dependent manner, and in the group (F/GSE #10 50) treated with ginseng seed extract, which is a comparative example of the present disclosure, the fatigue relief effect was shown to be minimal. This ginseng seed extract itself contains trace amount of the novel ginsenoside GS #10 as well as no other anti-fatigue substance. This indicates that the anti-fatigue efficacy is a unique feature of the novel ginsenoside GS #10 of one embodiment of the present disclosure.

Hereinafter, formulation examples of the composition according to one embodiment of the present specification will be explained. However, the formulation examples can be applied to various other formulations and are not intended to limit the present specification but only to specifically explain the present disclosure.

[Formulation Example 1] Tablet 100 mg of ginsenoside PG-$RT_8$, 400 mg of lactose, 400 mg of corn starch, and 2 mg of magnesium stearate were mixed, and then tableted to prepare a tablet in accordance with a conventional method for preparing tablets.

[Formulation Example 2] Capsule 100 mg of Ginsenoside PG-$RT_8$100 mg, 400 mg of lactose, 400 mg of corn starch, and 2 mg of magnesium stearate were mixed, and then filled into gelatin capsules to prepare a capsule in accordance with a conventional method for preparing capsules.

[Formulation Example 3] Granule 100 mg of ginsenoside PG-$RT_8$, 250 mg of anhydrous glucose and 550 mg of starch were mixed, molded into granules using a fluidized bed granulator, and then filled into a pouch.

[Formulation Example 4] Drink 50 mg of ginsenoside PG-$RT_8$, 10 g of glucose, 0.6 g of citric acid, and 25 g of liquid oligosaccharides were mixed, added with 300 ml of purified water, and 200 ml of the mixture was filled in a bottle. After the bottle was filled, the content was sterilized at 130° C. for 4-5 seconds to prepare a drink.

[Formulation Example 5] Caramel Formulation 50 mg of ginsenoside PG-$RT_8$, 1.8 g of corn syrup, 0.5 g of skim milk, 0.5 g of soy lecithin, 0.6 g of butter, 0.4 g of vegetable hardened oil, 1.4 g of sugar, 0.58 g of margarine, and 20 mg of table salt were mixed to prepare caramel.

[Formulation Example 6] Health Food

TABLE 3

| Components | Contents |
|---|---|
| PG-RT$_8$ | 100 mg |
| Vitamin mixture | |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Mineral mixture | |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

Although the composition ratio of the vitamin and inorganic mixture was obtained by a mixed composition using the components that are relatively suitable for health foods, it is irrelevant to arbitrarily modify the compounding ratio for carrying out the present disclosure. The above ingredients may be mixed according to the conventional method for preparing health foods, and then may be used for preparing a granule and preparing a health food composition according to the conventional method.

[Formulation Example 7] Healthy Drink

TABLE 4

| Components | Contents |
|---|---|
| PG-RT$_8$ | 10 mg |
| Citric acid | 1000 mg |
| Oligosaccharide | 100 g |
| Plum concentrate | 2 g |
| Taurine | 1 g |
| Purified water | Balance |
| Total volume | 900 Ml |

As shown in the table above, a balance of purified water was added to make a total volume of 900 ml, and the above components were mixed according to the conventional method for preparing a healthy drink, stirred and heated at 85° C. for about 1 hour, and then the resulting solution was filtered, obtained in a sterilized 2-liter container, sterilized sealed, and then refrigerated to prepare a healthy beverage composition.

[Formulation Example 8] Injection

Injections were prepared by conventional methods according to the compositions described in the table below.

TABLE 5

| Compounding components | Contents (wt %) |
|---|---|
| PG-RT$_8$ | 10-50 mg |
| Sterile distilled water for injection | Proper amount |
| pH regulator | Proper amount |

The present disclosure may provide the following embodiments as an example.

In a first embodiment, there may be provided a method of enhancing exercise ability or anti-fatigue comprising administering to a subject in need thereof an effective amount of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

In a second embodiment, in accordance with the first embodiment, there may be provided a method, wherein the (20S,24R)-6-O-β-D-glucopyranosyl(1→2)-3-D-glucopyranoside-dammar-3-one-20,24-epoxy-6a,12b,25-triol has the structure of following formula 1.

[Formula 1]

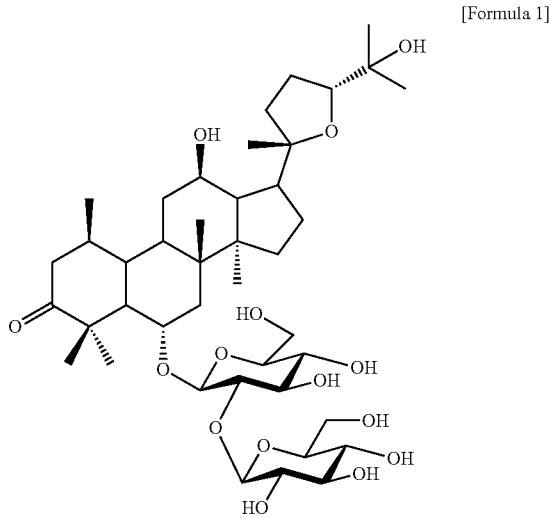

In a third embodiment, in accordance with the first or second embodiment, there may be provided a method, wherein the (20S,24R)-6-O-β-D-glucopyranosyl(1→2)-β-D-glucopyranoside-dammar-3-one-20,24-epoxy-6a,12b,25-triol is extracted from ginseng seed.

In a fourth embodiment, in accordance with any one or more of the first to third embodiments, there may be provided a method, wherein the method is for one or more of muscle regeneration promotion, muscle augmentation, muscle strengthening, the prevention or improvement of sarcopenia, and fatigue recovery promotion and lactic acid metabolism control.

In a fifth embodiment, in accordance with any one or more of the first to fourth embodiments, there may be provided a method, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate, or a solvate thereof promotes the production of mitochondria in myocytes.

In a sixth embodiment, in accordance with any one or more of the first to fifth embodiments, there may be provided a method, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate, or a solvate thereof promotes the fatty acid oxidation in myocytes.

In a seventh embodiment, in accordance with any one or more of the first to sixth embodiments, there may be provided a method, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate, or a solvate thereof reduces the plasma lactate in blood produced by exercise In an eighth embodiment, in accordance with any one or more of the first to seventh embodiments, there may be provided a method, wherein the dose of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate, or a solvate thereof is 0.05 mg/kg/day to 10 g/kg/day.

In a ninth embodiment, in accordance with any one or more of the first to eighth embodiments, there may be provided a method, wherein the method comprises a transdermal administration of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

In a tenth embodiment, in accordance with any one or more of the first to ninth embodiments, there may be provided a method, wherein the method comprises an oral or parenteral administration of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

The above embodiments have been disclosed for the purposes of illustration, and the description is not intended to limit the scope of the present disclosure. Accordingly, various modifications, variations, and substitutions may occur to those skilled in the art without departing from the spirit and scope of the present disclosure.

What is claimed is:

1. A method of enhancing exercise ability or anti-fatigue comprising administering to a subject in need thereof an effective amount of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

2. The method of claim 1, wherein the (20S,24R)-6-O-β-D-glucopyranosyl(1→2)-β-D-glucopyranoside-dammar-3-one-20,24-epoxy-6a,12b,25-triol has the structure of following formula 1:

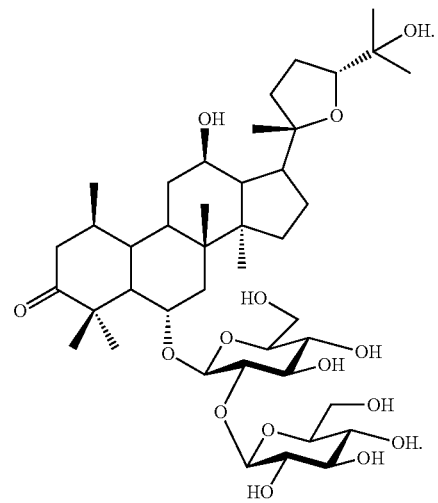

[Formula 1]

3. The method of claim 1, wherein the (20S,24R)-6-O-β-D-glucopyranosyl(1→2)-β-D-glucopyranoside-dammar-3-one-20,24-epoxy-6a,12b,25-triol is extracted from ginseng seed.

4. The method of claim 1, wherein the method is for one or more of muscle regeneration promotion, muscle augmentation, muscle strengthening, the prevention or improvement of sarcopenia, and fatigue recovery promotion and lactic acid metabolism control.

5. The method of claim 1, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate, or a solvate thereof promotes the production of mitochondria in myocytes.

6. The method of claim 1, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate, or a solvate thereof promotes the fatty acid oxidation in myocytes.

7. The method of claim 1, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate, or a solvate thereof reduces the plasma lactate in blood produced by exercise.

8. The method of claim 1, wherein the dose of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate, or a solvate thereof is 0.5 mg/kg/day to 10 g/kg/day.

9. The method of claim 1, wherein the method comprises transdermal administration of the (20S,24R)-6-O-β-D-glucopyranosyl(1→2)-3-D-glucopyranoside-dammar-3-one-20,24-epoxy-6a,12b,25-triol, a pharmaceutically acceptable salt thereof, a hydrate, or a solvate thereof.

10. The method of claim 1, wherein the method comprises oral or parenteral administration of the (20S,24R)-6-O-β-D-glucopyranosyl(1→2)-3-D-glucopyranoside-dammar-3-one-20,24-epoxy-6a,12b,25-triol, a pharmaceutically acceptable salt thereof, a hydrate or a solvate thereof.

* * * * *